(12) United States Patent
Zupancic et al.

(10) Patent No.: US 9,469,614 B2
(45) Date of Patent: Oct. 18, 2016

(54) SYNTHESIS OF TRIAZOLOPYRIMIDINE COMPOUNDS

(71) Applicant: Lek Pharmaceuticals d.d., Ljubljana (SI)

(72) Inventors: Borut Zupancic, Ljubljana (SI); Nenad Maras, Ljubljana (SI); Damjan Sterk, Ljubljana (SI)

(73) Assignee: Lek Pharmaceuticals d.d. (SI)

( * ) Notice: Subject to any disclaimer, the term of this patent is extended or adjusted under 35 U.S.C. 154(b) by 47 days.

(21) Appl. No.: 14/353,885

(22) PCT Filed: Oct. 26, 2012

(86) PCT No.: PCT/EP2012/071252
§ 371 (c)(1),
(2) Date: Apr. 24, 2014

(87) PCT Pub. No.: WO2013/060837
PCT Pub. Date: May 2, 2013

(65) Prior Publication Data
US 2014/0256747 A1    Sep. 11, 2014

(30) Foreign Application Priority Data

Oct. 27, 2011 (EP) .................................. 11186817
Dec. 23, 2011 (EP) .................................. 11195608

(51) Int. Cl.
*C07D 487/04* (2006.01)
*C07D 239/46* (2006.01)
*C07D 239/56* (2006.01)
*C07D 405/12* (2006.01)

(52) U.S. Cl.
CPC ............ *C07D 239/46* (2013.01); *C07D 239/56* (2013.01); *C07D 405/12* (2013.01); *C07D 487/04* (2013.01)

(58) Field of Classification Search
CPC .................................................... C07D 487/04
See application file for complete search history.

(56) References Cited

U.S. PATENT DOCUMENTS 6,251,910 B1    6/2001  Guile et al.

FOREIGN PATENT DOCUMENTS

| WO | 0034283 A1 | 6/2000 |
| WO | 0192263 A1 | 12/2001 |
| WO | 2010-030224 A1 | 3/2010 |
| WO | 2011-017108 A2 | 2/2011 |

OTHER PUBLICATIONS

Springthorpe, "From ATP to AZD6140: The discovery of an orally active reversible P2Y12 receptor antagonist for the prevention of thrombosis," Science Direct, Bioorganic & Medicinal Chemistry Letters 17 (2007) 6013-6018.

*Primary Examiner* — Brian McDowell
(74) *Attorney, Agent, or Firm* — Luedeka Neely Group, P.C.

(57) ABSTRACT

The present invention relates to the field of organic synthesis and describes the synthesis of specific triazolopyrimidine compounds and intermediates thereof as well as related derivatives.

2 Claims, No Drawings

SYNTHESIS OF TRIAZOLOPYRIMIDINE COMPOUNDS

This application is a national phase entry of PCT International application number PCT/EP2012//071252, filed Oct. 26, 2012. This application also claims the benefit of the earlier filing dates of: (1) EP11186817.0, filed Oct. 27, 2011; and (2) EP11195608.2, filed Dec. 23, 2011.

The present invention relates to the field of organic synthesis, in particular to the synthesis of specific triazolopyrimidine compounds and intermediates thereof as well as related derivatives.

BACKGROUND OF INVENTION

An important triazolopyrimidine compound is ticagrelor (TCG; Brilinta®; 3-[7-[[(1R,2S)-2-(3,4-difluorophenyl)cyclopropyl]amino]-5-(propylthio)-3H-1,2,3-triazolo[4,5-d]pyrimidin-3-yl]-5-(2-hydroxyethoxy)-(1S,2S,3R,5S)-1,2-cyclopentanediol) having the following structural formula.

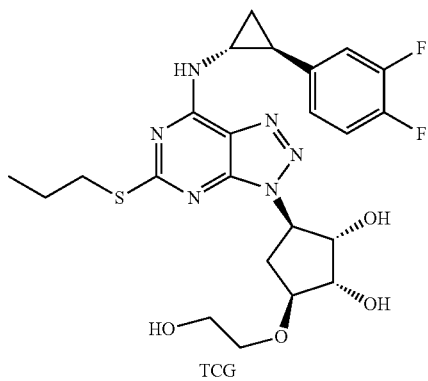 [SMILES: CCCSc1nc(N[C@@H]2C[C@H]2c2ccc(F)c(F)c2)c2nnn([C@@H]3C[C@H](OCCO)[C@@H](O)[C@H]3O)c2n1]

TCG

Ticagrelor shows pharmaceutical activity by functioning as a P2Y12 receptor antagonist and thus is indicated for the treatment or prevention of thrombotic events, for example stroke, heart attack, acute coronary syndrome or myocardial infection with ST elevation, other coronary artery diseases and arterial thrombosis as well as other disorders related to platelet aggregation (WO 00/34283).

The synthesis of ticagrelor (TCG) is demanding. There are five to six known synthetic variants, which are described in the basic patent application WO 00/34283, an improved one in patent application WO 01/92263, and a further improved one in patent application WO 10/030,224 respectively derived from the originator AstraZeneca, while two are published in a "deutero" patent application WO 11/017,108 of Auspex Pharmaceuticals. Further, there is one synthetic path published in a scientific journal (*Bioorg. Med. Chem. Lett.* 2007, 17, 6013-6018).

The first synthesis of TCG as described in WO 00/34283 is depicted in scheme 1 below.

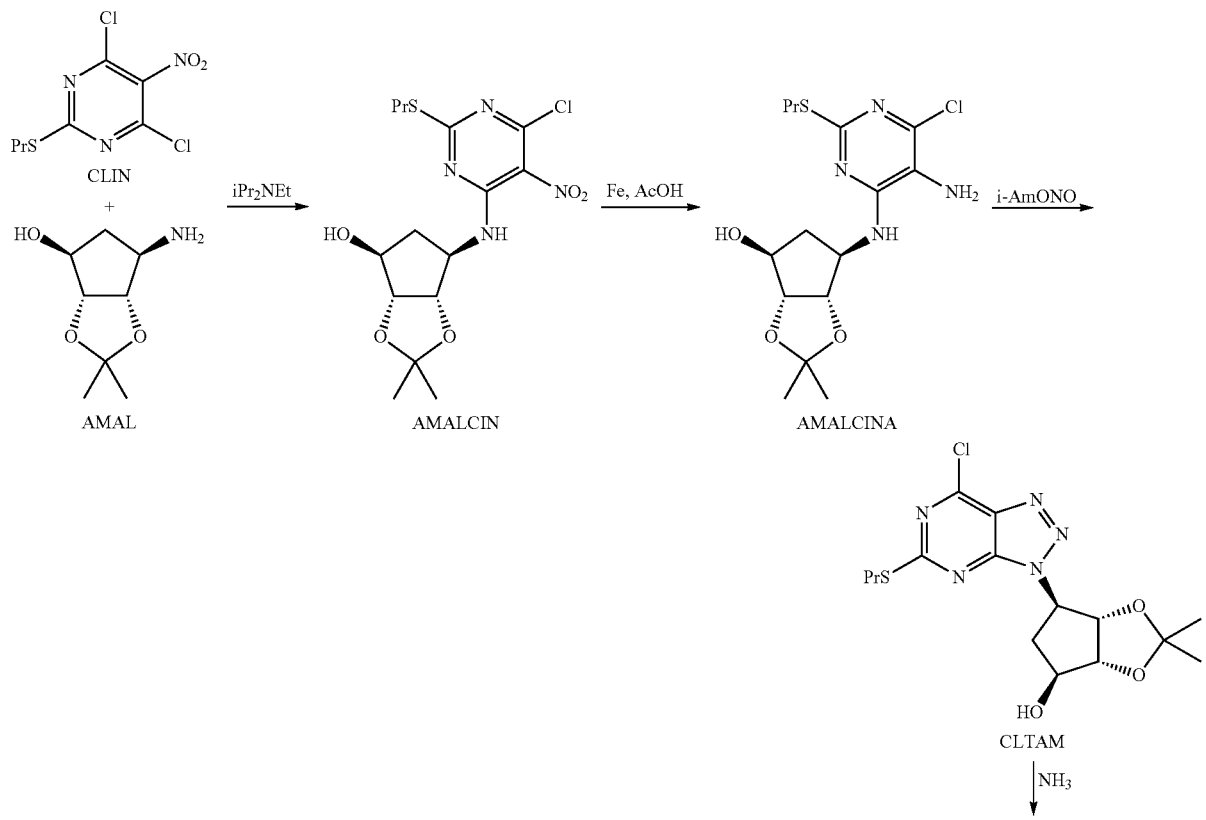

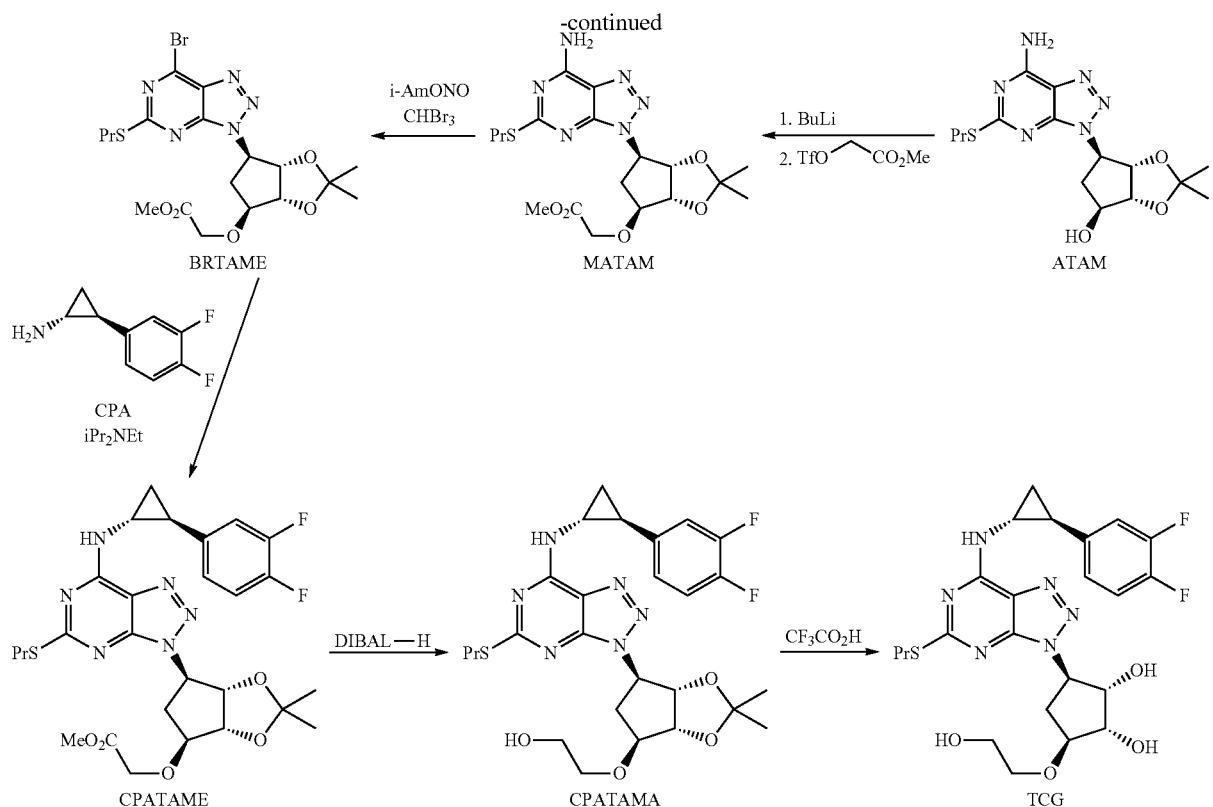

This nine step synthesis of ticagrelor (TCG) as described in WO 00/34283 (Scheme 1) starts with a reaction between CLIN and AMAL. In the presence of diizopropylethylamine (iPr$_2$Net) AMALCIN is formed, which is in then reduced with iron (Fe) in acetic acid to AMALCINA. In the next step CLTAM is formed using isopentyl nitrite (iAmONO). Next, ATAM was prepared using ammonia, and side chain was introduced (MATAM) using n-butyllithium and methyl 2-(((trifluoromethyl)sulfonyl)oxy)acetate, which was previously prepared by reaction between methyl glycolate and triflic anhydride. In next step BRTAME is formed using iAmONO and CHBr$_3$, followed by the aromatic nucleophilic substitution of Br with CPA in the presence of iPr$_2$NEt to form CPATAME. This is than reduced to CPATAMA using DIBAL-H. Deprotection of diol group in the presence of trifluoroacetic acid in the final step leads to TCG. This synthetic path is very long (9 steps, not including reagents preparation) and uses toxic compounds like CHBr$_3$, triflic anhydride, and methyl 2-(((trifluoromethyl)sulfonyl)oxy)acetate.

An improved synthesis of ticagrelor (TCG) is described in WO 01/92263 (see Scheme 2). In this process the hydroxyethyl side chain is introduced at the beginning of the synthesis by a three step reaction path from AMAL to AMALA, which is then reacted with CLINA (prepared from CLIDA) in presence of triethylamine (Et$_3$N) to form AMALCINAA. The triazole ring of CLTAM is formed with NaNO$_2$ in acetic acid, and then Cl is exchanged with CPA to form CPATAMA. In the final step TCG is prepared via deprotection using NCl.

This improved process still has substantial length (7-8 steps). In AMALA synthesis the benzyloxycarbonyl protection (Cbz) is used, which is then removed in the third step using hydrogenation with Pd/C as a catalyst. Also, hydrogenation with Pt/C as a catalyst is used in the reduction of CLIDA to CLINA.

Scheme 2: Synthesis of ticagrelor (TCG) as described in WO 01/92263.

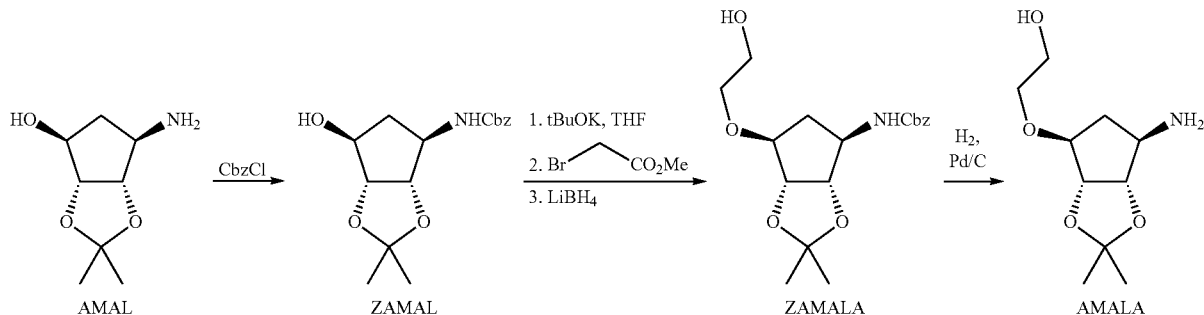

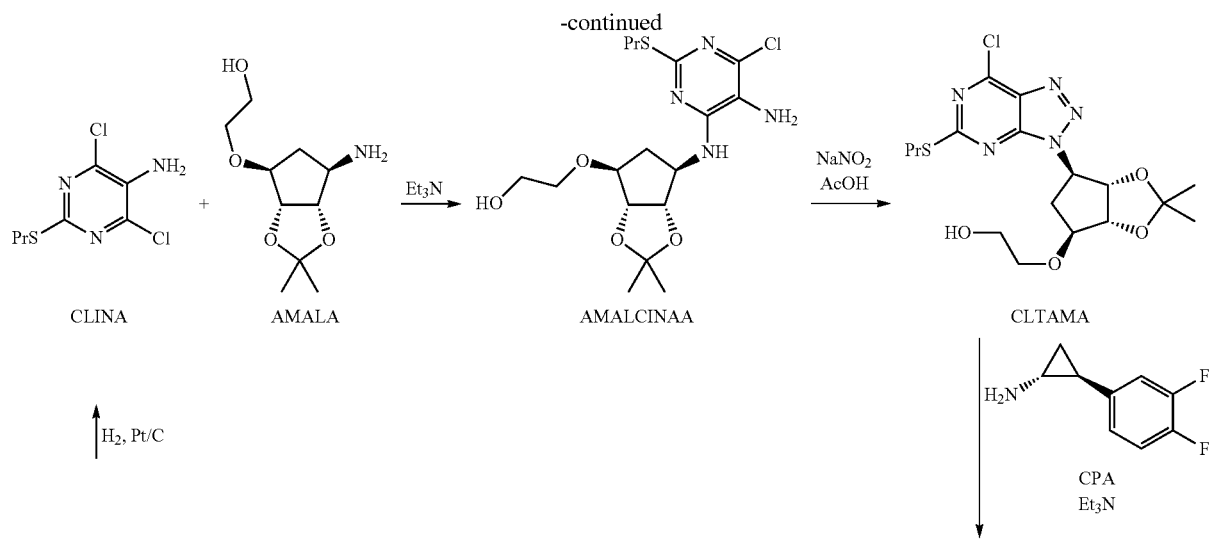

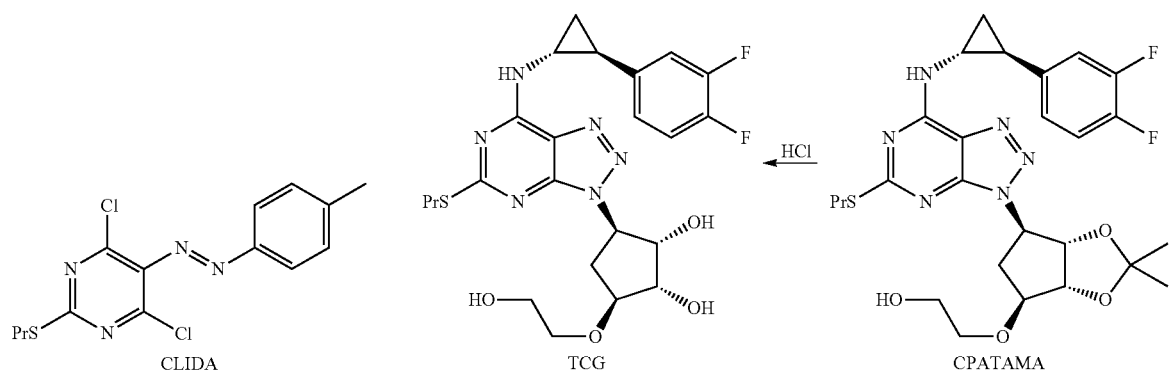

Another improved synthetic path is described in WO 10/030,224 (Scheme 3). The key steps in this process are reduction of CLIN to CLINA or AMALCINO to AMALCINAA using hydrogen gas and platinum vanadium catalyst. The introduction of the hydroxyethyl side chain to AMAL to form AMALA, cyclization, substitution of Cl atom of CLTAMA with CPA and final acidic deprotection are the same as in WO 01/92263.

This further improved process to TCG has 8 reaction steps. Like in WO 01/92263, there are used the Cbz protecting group and heavy metals as catalysts like Pd, Pt and/or V.

Scheme 3: Syntheses of ticagrelor (TCG) as described in WO 10/030224.

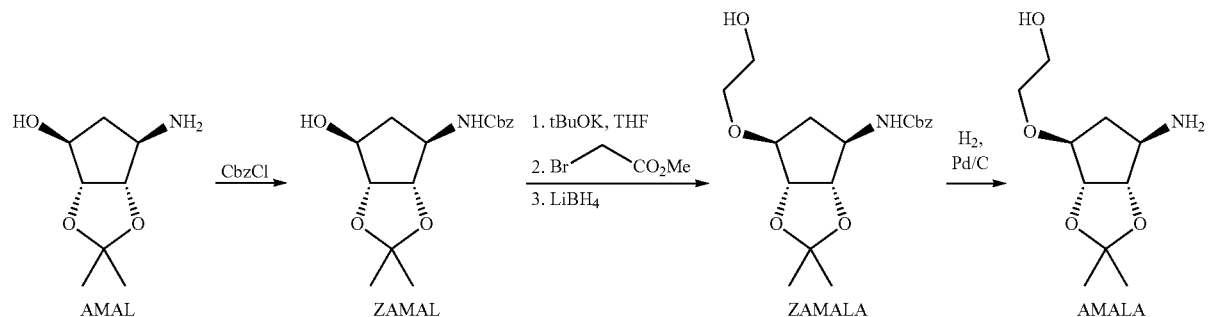

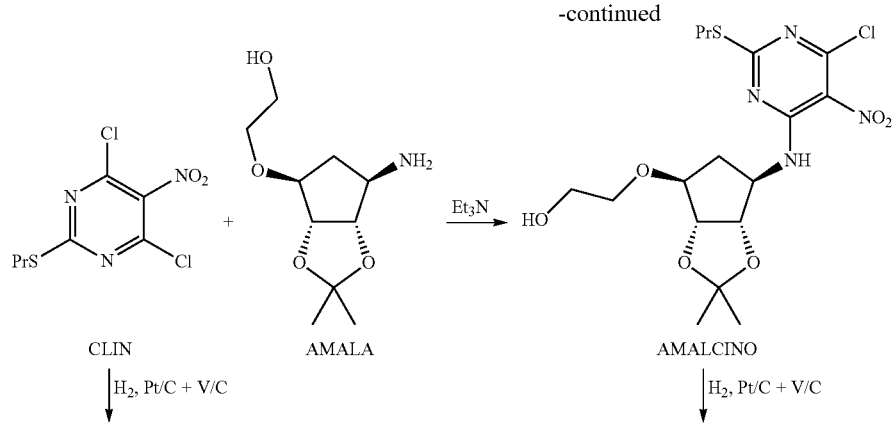
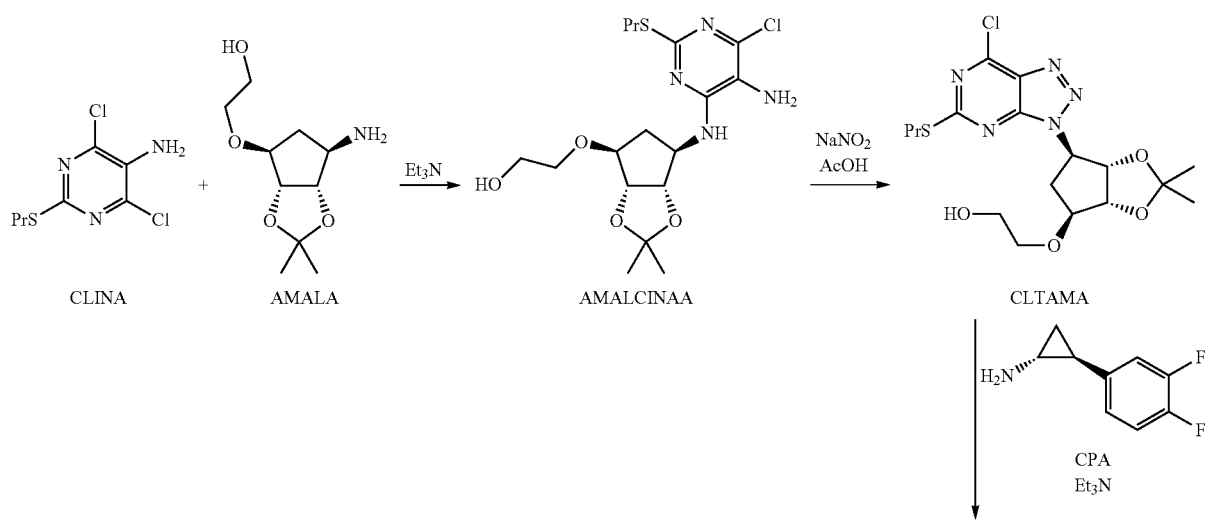
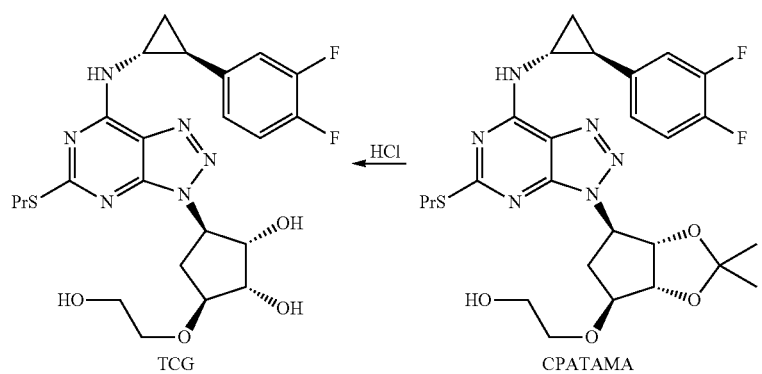
AstraZeneca published a synthetic path (Scheme 4) to ticagrelor (TCG) in *Bioorg. Med. Chem. Lett.* 2007, 17, 6013-6018. Intermediates in this process are similar to those described in WO 01/92263. There is difference in formation of triazolo ring of CLTAMA where iAmONO is used, and difference in deprotection in the last step.

Scheme 4: Synthesis of ticagrelor (TCG) as described in *Bioorg. Med. Chem. Lett.* 2007, 17, 6013-6018.

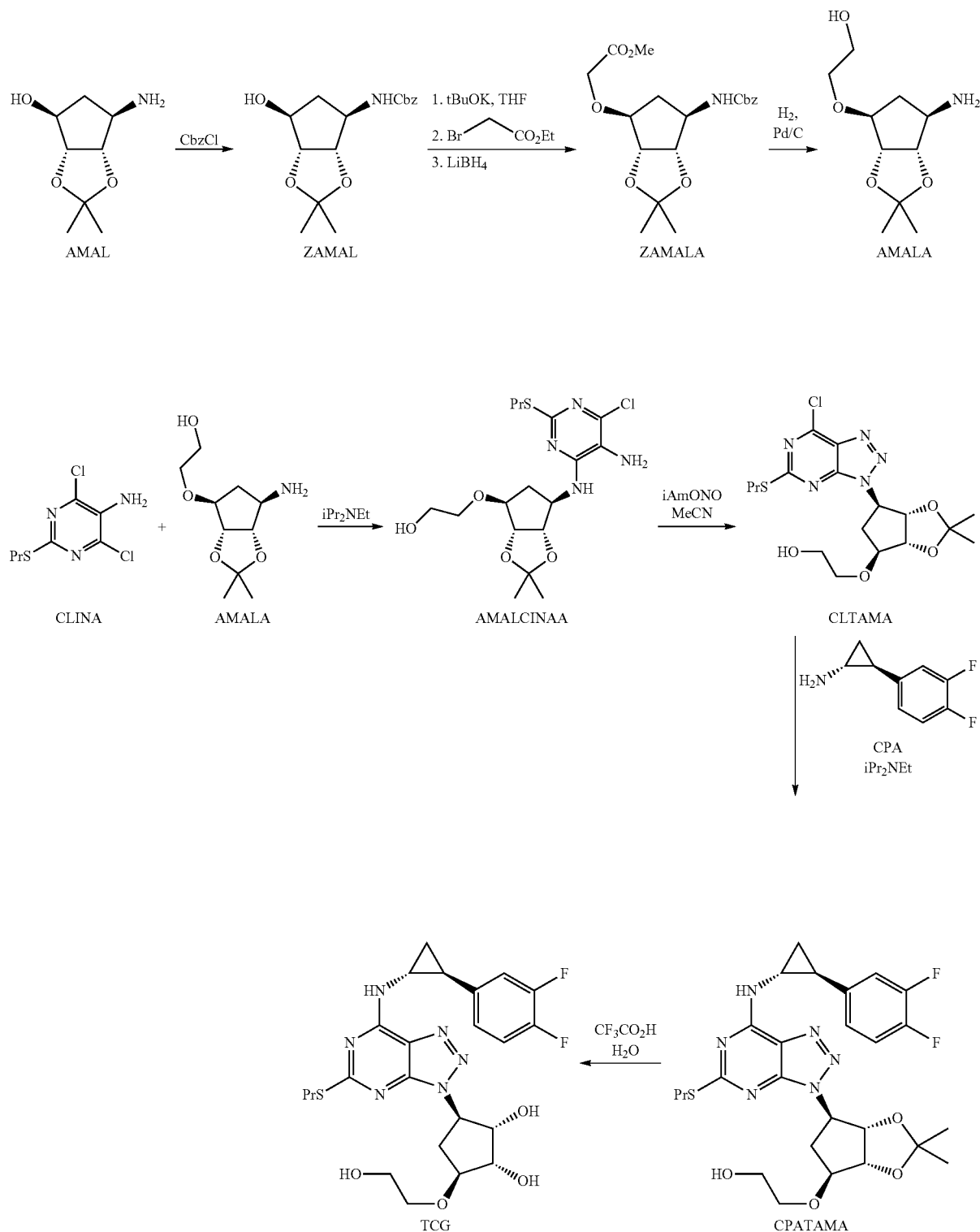

Another synthetic variant (Scheme 5) to ticagrelor (TCG) is described in WO 11/017,108 by Auspex Pharmaceuticals. In nine step synthesis they prepared AMALE through deprotection of ZAMALE using hydrogen gas and Pd/C, which was then reduced to AMALA with LiAlH$_4$. AMALCINO was prepared without presence of base, further steps are similar to those published in WO 01/92263.

Still another synthetic variant (Scheme 6) to obtain ticagrelor with deuterated hydroxyethyl group (TCGD) is also described in WO 11/017,108 by Auspex Pharmaceuticals.

Scheme 5: Synthesis of ticagrelor (TCG) as described in "deutero" patent WO 11/017108.
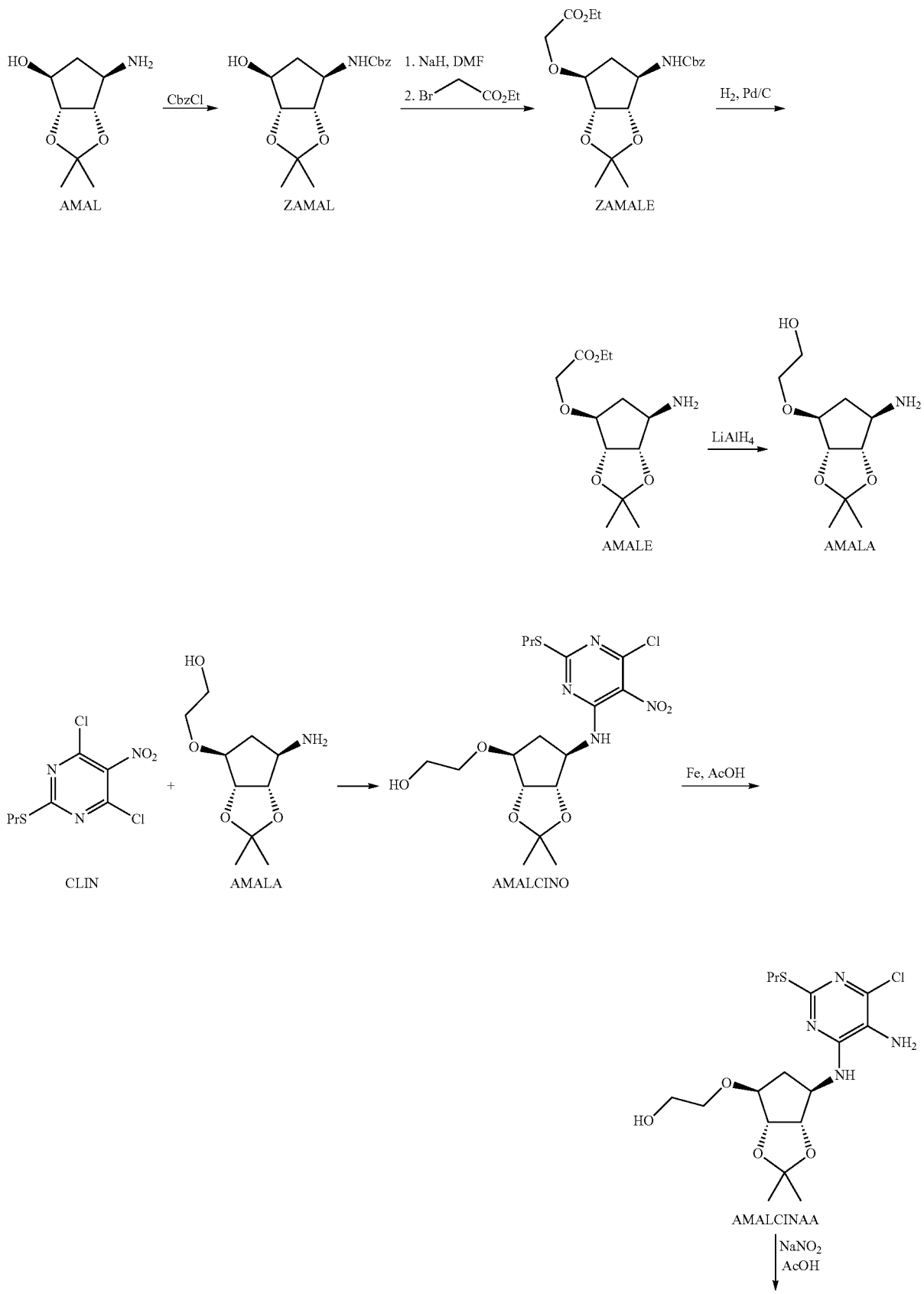

-continued
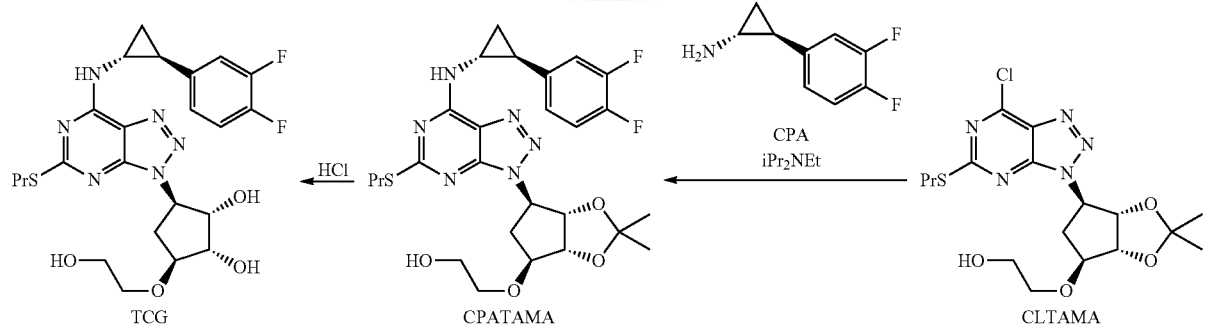
Scheme 6: Synthesis of ticagrelor with deuterated hydroxyethyl group (TCGD) as described in "deutero" patent WO 11/017108.
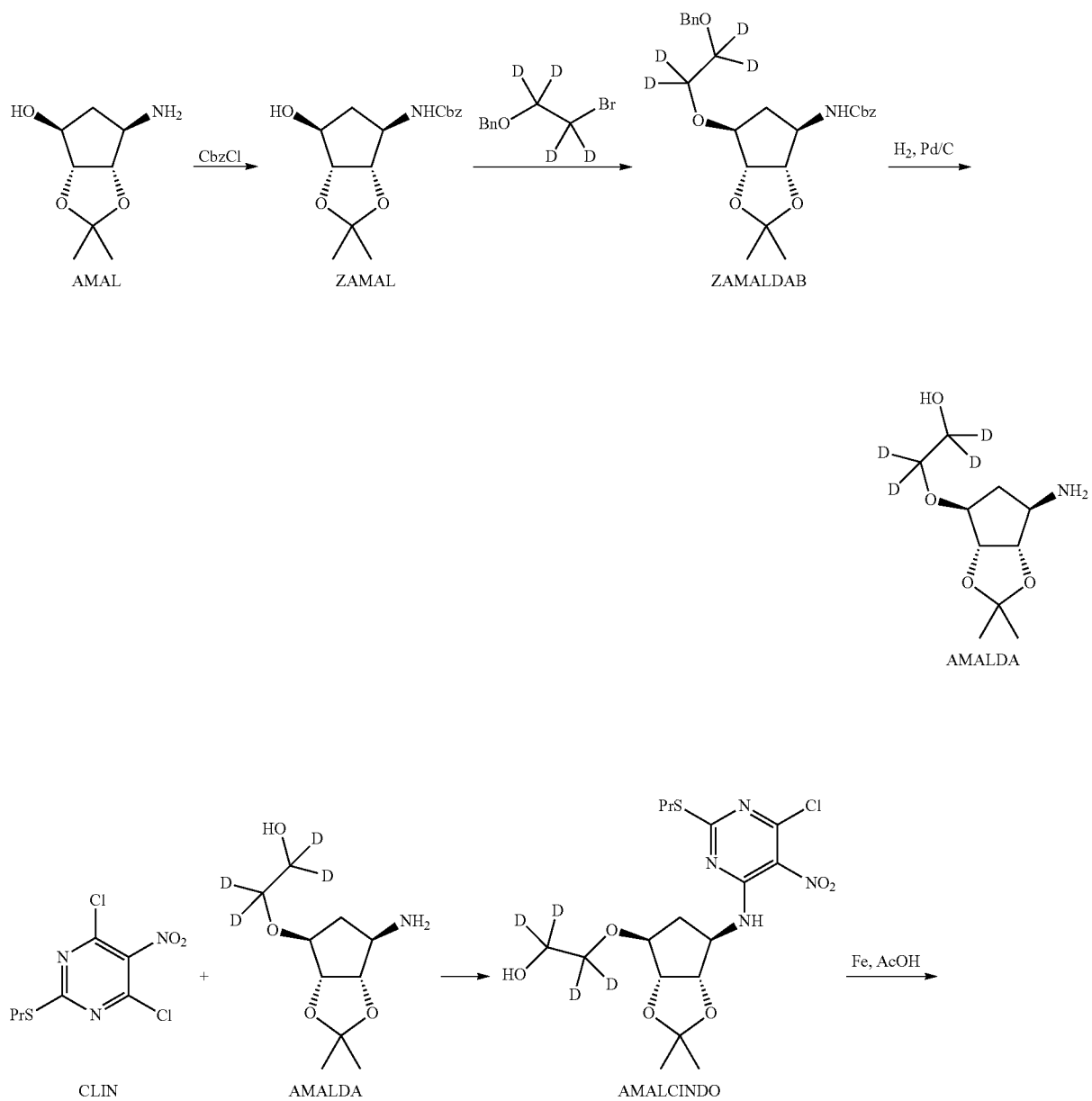

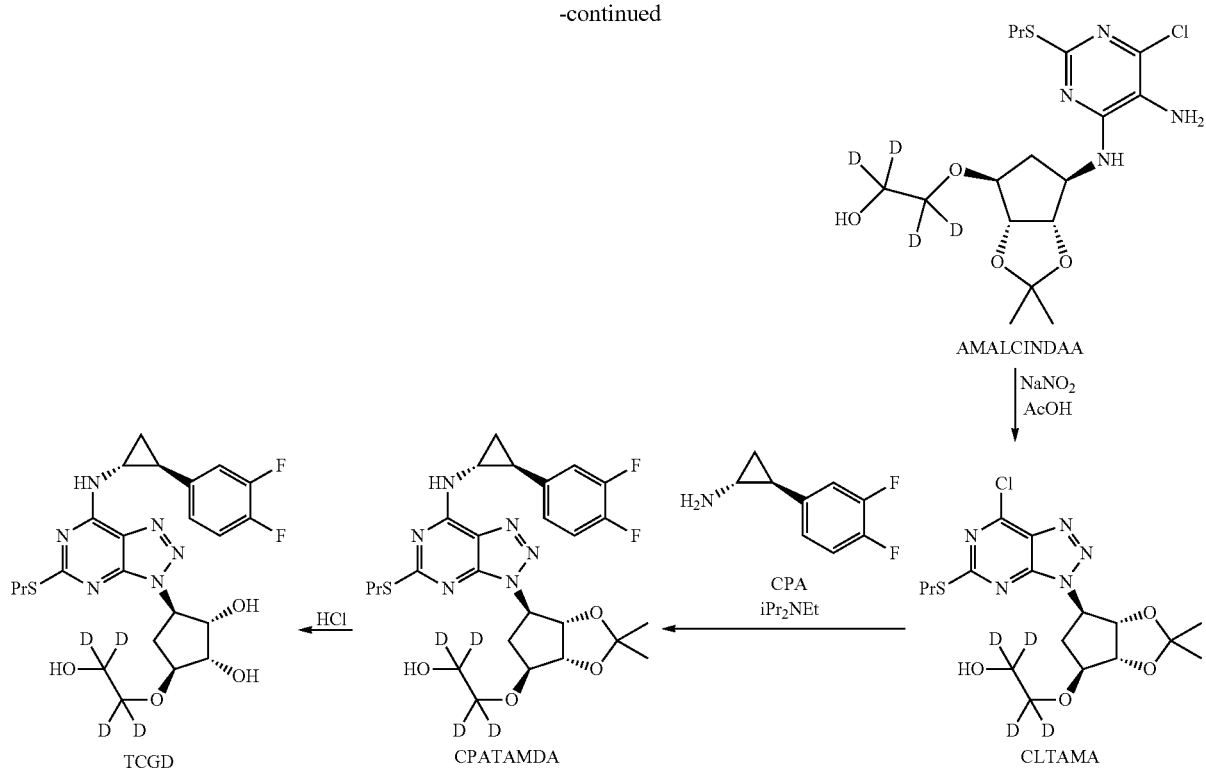

O-alkylation of the secondary alcohol functional group is often a demanding step for which a strong base such as sodium hydride is needed. The chemoselectivity problem arises in the presence of the reactive heteroaryl chloride functionality, because the oxy anion formed may attack the position of chloro atom ("selfarylation") leading to considerable amounts of by-products (Scheme 7). In the known procedure, published in WO 00/34283 and represented in Scheme 1 the unwanted side reaction is avoided by first changing the reactive halogen to amino group, than conducting alkylation step and finally converting amino group back to halo group.

Alternatively, hydroxyethyl group can be introduced by alkylation of cyclopentane part before heteroarylation as presented in upper parts of Schemes 2 to 6. However, in order to alkylate hydroxy group in the presence of an amino group the nitrogen atom must be protected.

Scheme 7 showing the chemoselectivity issue in case of O-alkylation of the secondary alcohol functional group in which strong base is needed.

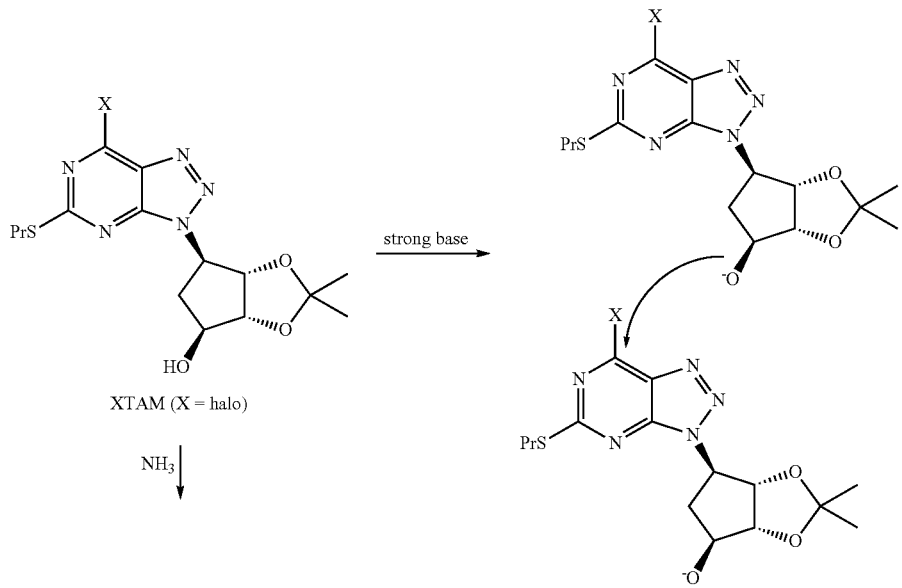

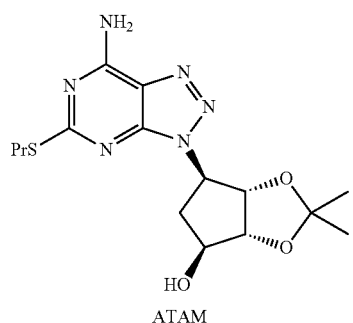

ATAM strong base
alkylation

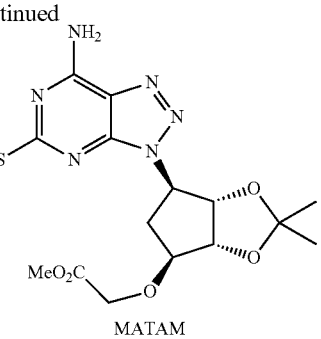

MATAM halogen introducing
reaction

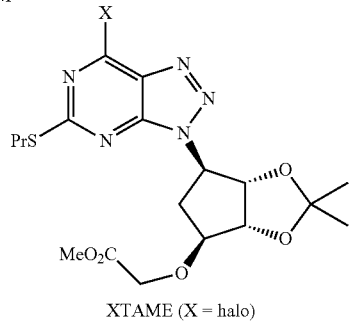

XTAME (X = halo)

As becomes apparent from the above, a major drawback of the hitherto known synthesis schemes for the preparation of ticagrelor is that the synthesis is long.

SUMMARY OF THE INVENTION

The object of the present invention was to provide an industrially applicable and economically improved process for obtaining ticagrelor.

The present invention provides a process for the preparation of a compound of formula VIII

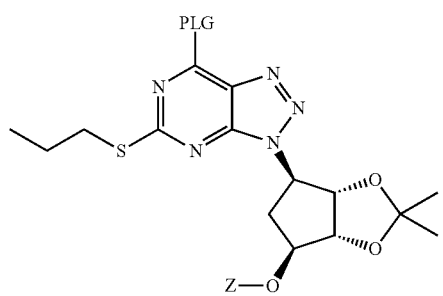

wherein PLG is a protecting-leaving group, and Z is hydroxyethyl or a group convertible to hydroxyethyl, the process comprising the steps of:
(i) providing a compound of formula VII

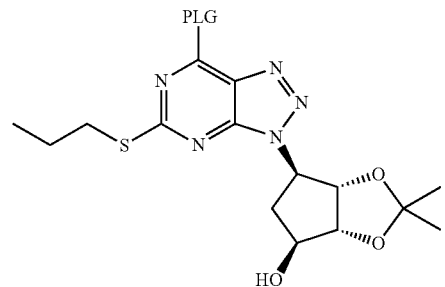

wherein PLG is defined as above, and
(ii) O-alkylating the compound of formula VII to obtain the compound of formula VIII.

The process defined above allows for preparation or synthesis of ticagrelor with an industrially applicable and economically improved process. Preferred embodiments will be described below. The present invention further provides novel compounds that are highly useful as key intermediates in the preparation or synthesis of ticagrelor.

DESCRIPTION OF THE INVENTION AND OF PREFERRED EMBODIMENTS

Aspects, advantageous features and preferred embodiments of the present invention will be described in further detail below, noting however that such aspects, advantages features as well as embodiments and examples are presented for illustrative purposes only and shall not limit the invention in any way.

The introduction of the so called "protecting-leaving group" on the position 6 or 7 of the pyrimidine or triazolo-pyrimidine ring, respectively, of the intermediates in the synthesis of ticagrelor is a significant point of the present invention, which is a novel feature common to the key steps of the synthetic preparation of ticagrelor as well as to the intermediate compounds thereof. This crucial point, which distinguishes significantly over all prior art synthesis, allows that the hydroxyethyl group can be introduced in a later stage of the ticagrelor molecular assembly.

The "protecting-leaving group" (PLG) is a multipurpose single functional group which is able to serve as a protecting group in some chemical reactions, and then as a leaving group in a later reaction step. The role such a group takes depends on the reaction applied. There is a number of substitutions that can properly moderate the reactivity of the electron poor heteroaryl moiety while still allowing a subsequent nucleophilic aromatic substitution to occur. The PLG finely balances the reactivity in order to allow several transformations. Most suitably, the protecting-leaving group PLG is both capable of acting as a protecting group in the O-alkylation reaction (ii) mentioned above and capable of acting as a leaving group when it will be subjected to a nucleophilic substitution reaction. Halogen (notably Cl or Br) is excluded as PLG.

The group convertible to hydroxyethyl ("Z") according to the invention can be selected from the group consisting of: —$CH_2COOR_1$, wherein $R_1$ is selected from linear or branched $C_1$-$C_6$-alkyl or benzyl; cyanomethyl; —$CH_2CH(E_1R_2)(E_2R_3)$, wherein $E_1$ and $E_2$ are independently selected from a chalcogen element, preferably O or S, and $R_2$ and $R_3$ are the same or different, selected from $C_1$-$C_4$-alkyl, or together form $C_2$-$C_4$-alkylene or o-phenylene connection; or —$CH_2CH_2$—$OR_4$ wherein $R_4$ is a hydroxy protecting group, selected from tertiary alkyl group, preferably tert-butyl or trityl, arylmethyl group, preferably benzyl or para substituted benzyl, methoxy substituted $C_1$-$C_2$-alkyl group, preferably methoxymethyl (MOM), trisubstituted silyl group, preferably trimethylsilyl, tert-butyldimethylsilyl (TBDMS) or tert-butyldiphenylsilyl, acyl, preferably acetyl or benzoyl.

In particular, the process according to the present invention reduces the number of the required steps. Contrary to the prior art processes, in which "protection/deprotection scenario" is followed, the so called "protection/leaving scenario" does not need any deprotection step because the PLG is simply exchanged with a wished substituent, meaning that the number of required reaction steps is reduced by one step. At the same time, an increase in reaction selectivity is achieved.

A further significant advantage of the present invention resides in the possibility that several steps can be performed through one-pot conversions, without the need of isolation or separation of intermediate compounds, which one-pot system therefore constitutes a preferred embodiment of the present invention.

Accordingly, the possibility of reducing the number of required reaction steps, of increasing reaction selectivity, and of simplifying reactions respectively strongly contributes to provide an improved industrially applicable and economically beneficial process for obtaining triazolopyrimidine compounds and specifically ticagrelor.

According to a preferred embodiment, the compound of formula VIIIa is prepared from the compound of formula VII, for example by the O-alkylation with an alkyl haloacetate or alkyl sulfonyloxyacetate and the reduction of the so formed ester in order to build a 2-hydroxyethyl side chain. In this reaction the protecting ability of PLG is demonstrated. The leaving group propensity is finally employed in the substitution by amine, in which VIIIa is reacting with IX to give CPATAMA. See Scheme 8.

Scheme 8 showing process embodiments of the present invention.

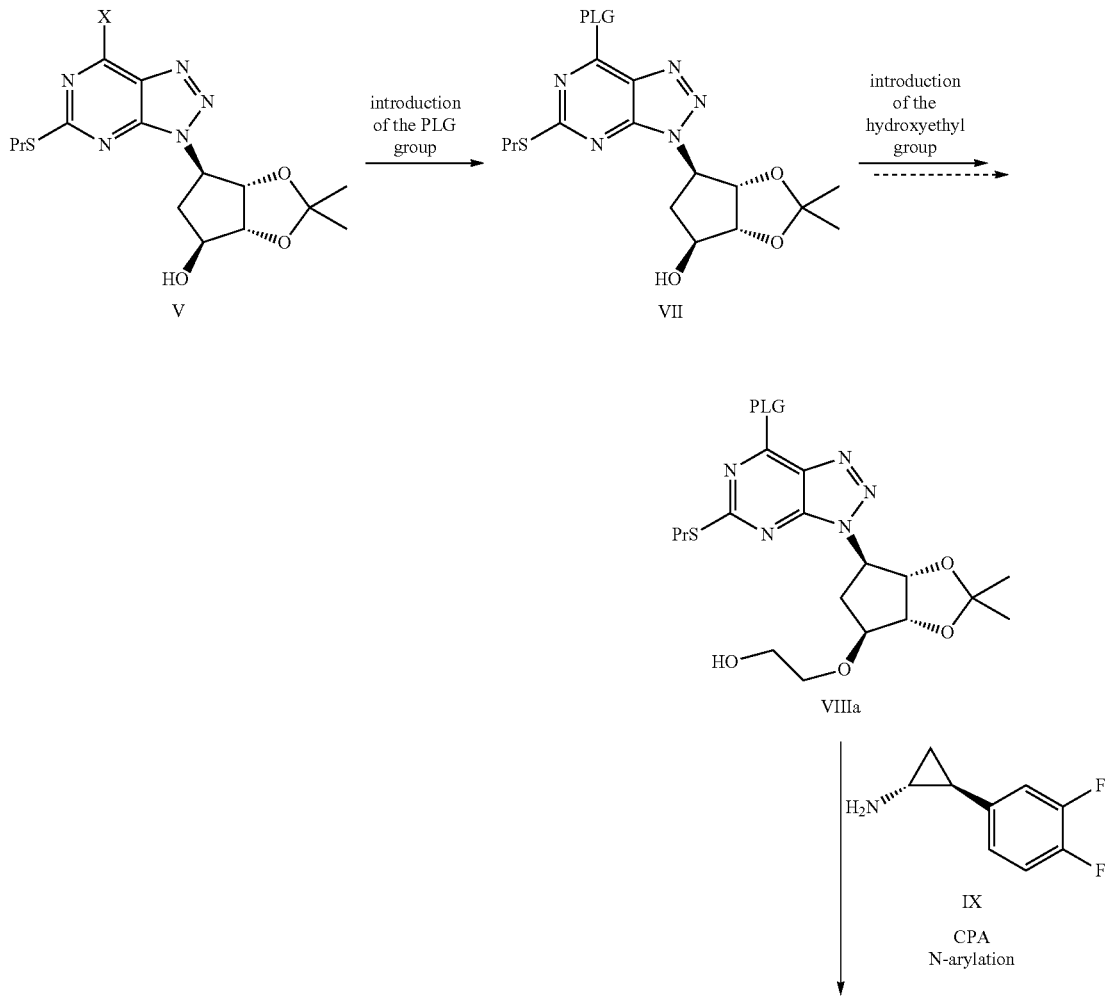

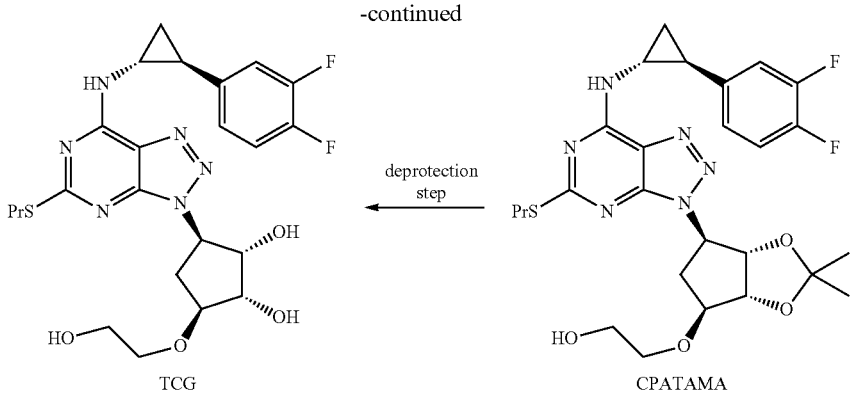

X...Cl, Br
PLG = "protecting-leaving" group
PLG = OR, OAr, SR, SAr, imidazole...

The PLG employed according to the present invention should provide properties that make the intermediates, for example a compound of formula VII, relatively stable in their deprotonated form at the reaction conditions required for the O-alkylation reaction, but at the same time it must impose reactivity for the subsequent reaction, in which an intermediate, for example a compound of formula VIIIa, reacts with an amine, for example a compound of formula IX (CPA). Optionally, the PLG can also be suitably selected to be stable under the ester group reduction conditions, when such a reaction is required in the building of the hydroxyethyl side chain.

It has been found that various functional groups possessing the above-mentioned properties can be efficiently introduced at different stages of ticagrelor synthesis. The protecting-leaving groups according to the present invention are selected from the group consisting of:

linear or branched $C_1$-$C_6$-alkoxy groups, optionally substituted with one or more aryl, heteroaryl, halo, $C_1$-$C_4$-alkoxy, $C_1$-$C_4$-alkylthio;

aryloxy or substituted aryloxy;

$C_8$-$C_{20}$-alkylthio, unsubstituted or substituted arylthio or heteroarylthio;

N-azolyl groups, selected from unsubstituted or substituted 1-imidazolyl, 1-pyrrolyl, 1-pyrazolyl, 1-indolyl, 1-(1,2,3-triazolyl), 1-(1,2,4-triazolyl), 4-(1,2,4-triazolyl), 1-tetrazolyl, 2-tetrazolyl, 1-benzopyrazolyl, 1-benzimidazolyl, 1-benzotriazolyl, 5-carbazolyl, 4-aza, 5-aza, 6-aza, 7-aza, 4,5-diaza, 4,6-diaza, 4,7-diaza, 5,6-diaza, 5,7-diaza, or 6,7-diaza derivatives of 1-benzopyrazolyl, 1-benzimidazolyl, or 1-benzotriazolyl;

N-amidyl groups selected from unsubstituted or substituted N-aryl-N—($C_1$-$C_6$-alkanoyl)amino, 3-(2-oxo-1,3-oxazolidinyl), 3-(2-oxo-1,3-benzoxazolidinyl), 2-oxo-1-(1,2-dihydropyridyl), 2-oxo-1-(1,2-dihydroquinolyl), 2-oxo-1-(1,2-dihydroquinazolyl);

1-benzotriazolyloxy;

azido; and cyano.

Halogen (notably Cl or Br) is excluded as PLG.

Representative types and examples of the protecting-leaving group are presented below.

Representative types and examples of the protection-leaving group (PLG):

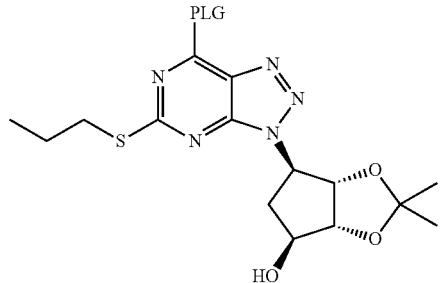

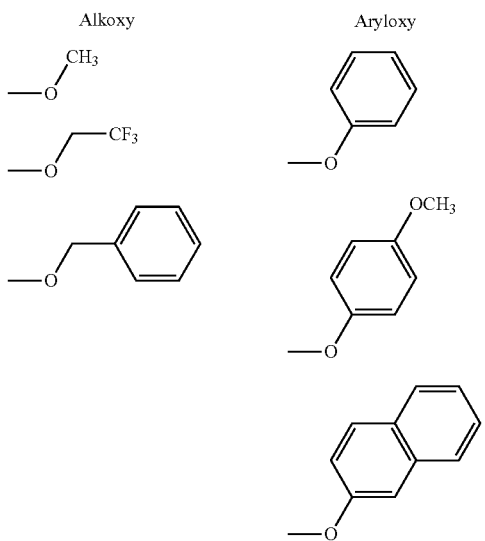

N-Azolyl -continued N-Amidyl    Thiolyl

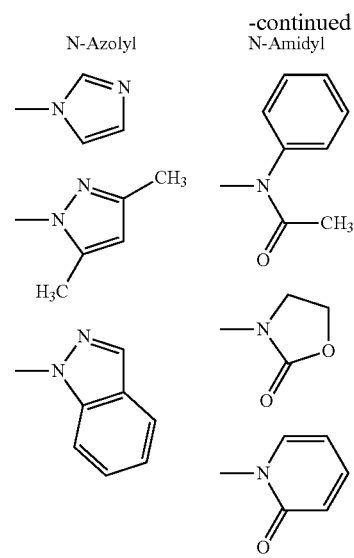

The protecting-leaving group, which is less reactive than halogen (notably Cl), preferably exerts particular resistance to O-nucleophiles. In view of industrial application, the PLG should be carefully selected in order to obtain high yields in O-alkylation reaction. The PLG should be inert during the conversion of the group convertible to hydroxyethyl into the hydroxyethyl group and in most preferred cases one or more reactions should be carried out in one pot. When PLG is a linear or branched $C_1$-$C_6$-alkoxy group, optionally substituted with one or more aryl, heteroaryl, halo. $C_1$-$C_4$-alkoxy, or $C_1$-$C_4$-alkylthio, yields of O-alkylation reaction higher than 50% are obtained. Most preferably the PLG is methoxy or benzyloxy, which provides for yields of alkylation reaction higher than 75% and thus represents an optimal balance between reactivity/inertness, yields and price. In addition, with higher yields, the level of impurities is lowered.

According to a preferred embodiment, the compound of formula VII is prepared by
(i) providing a compound of formula V

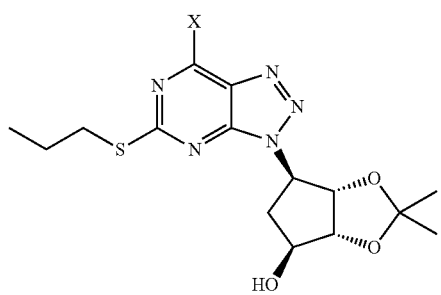

wherein X is Cl or Br, and
(ii) substituting X with PLG by reaction of a reagent PLG-H in the presence of a base, to obtain a compound of formula VII.

The compound of formula V can be prepared by
(i) providing a compound of formula I'

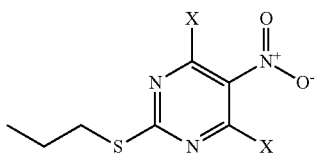

wherein X is Cl or Br,
(ii) reacting the compound of formula I' with a compound of formula III

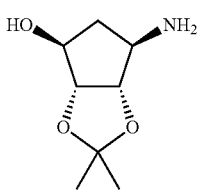

to obtain a compound of formula IV'

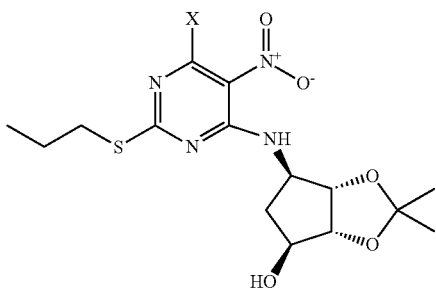

wherein X is as defined above,
(iii) reducing the nitro group of the compound of formula IV' to obtain a compound of formula IV"

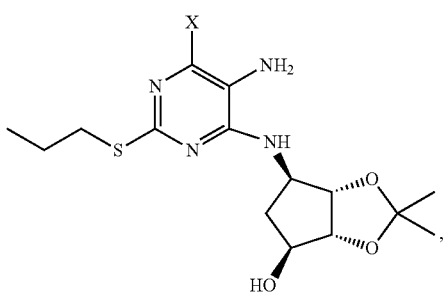

and
(iv) converting the compound of formula IV" into the compound of formula V by nitrosation.

In a characteristic part of the preferred embodiment of this invention shown in Scheme 9, PLG is introduced to heteroaryl halide V, for example heteroaryl chloride CLTAM (Va), by reaction of a reagent PLG-H in the presence of a base selected from the group consisting of metal or quaternary ammonium carbonates or phosphates, hydrogencarbonates, hydrogenphosphate, dihydrogenphosphate, hydroxides, alkoxides, hydrides, amides, alkyl metals or tertiary amines. The reaction is carried out at temperature from −20° C. to the reflux temperature, preferably at room temperature. The reaction medium depends on the nature of PLG group and consists of solvents in which reactants are at least partially soluble, which are compatible with the applied bases and which are inert in cases in which they do not contribute in the substitution of halo atom. Such solvents are selected from the group of alcohols, cyclic ethers, ketones, nitriles, amides, halogenated hydrocarbons, cyclic or acyclic carbonates and esters or mixture of thereof, or partially with the solvents of other groups such sulphoxides, acyclic ethers, aromatic or aliphatic hydrocarbons or water. The preferred medium for introduction of $C_1$-$C_6$-alkoxy group is the corresponding $C_1$-$C_6$-alcohol and alkali metal carbonate, phosphate or alkoxide as a base. For example, the intermediate MOTAM (VIIa) is prepared in methanol in the presence of potassium carbonate or sodium methoxide at room temperature. For the introduction of other groups, of which reagents cannot be used as a solvent, the preferred solvents are selected from cyclic ethers, such as tetrahydrofuran (THF), or methyltetrahydrofuran (MeTHF) or ketones, such as acetone. For example in the preparation of the aryl ether FOTAM (VIIb) the introduction of phenol is carried out in acetone in the presence of sodium carbonate, while in the characteristic example of preparation of the N-heteroarylimidazole IMTAM (VIIc) imidazole is introduced in THF or MeTHF and in the presence of triethylamine as a base.

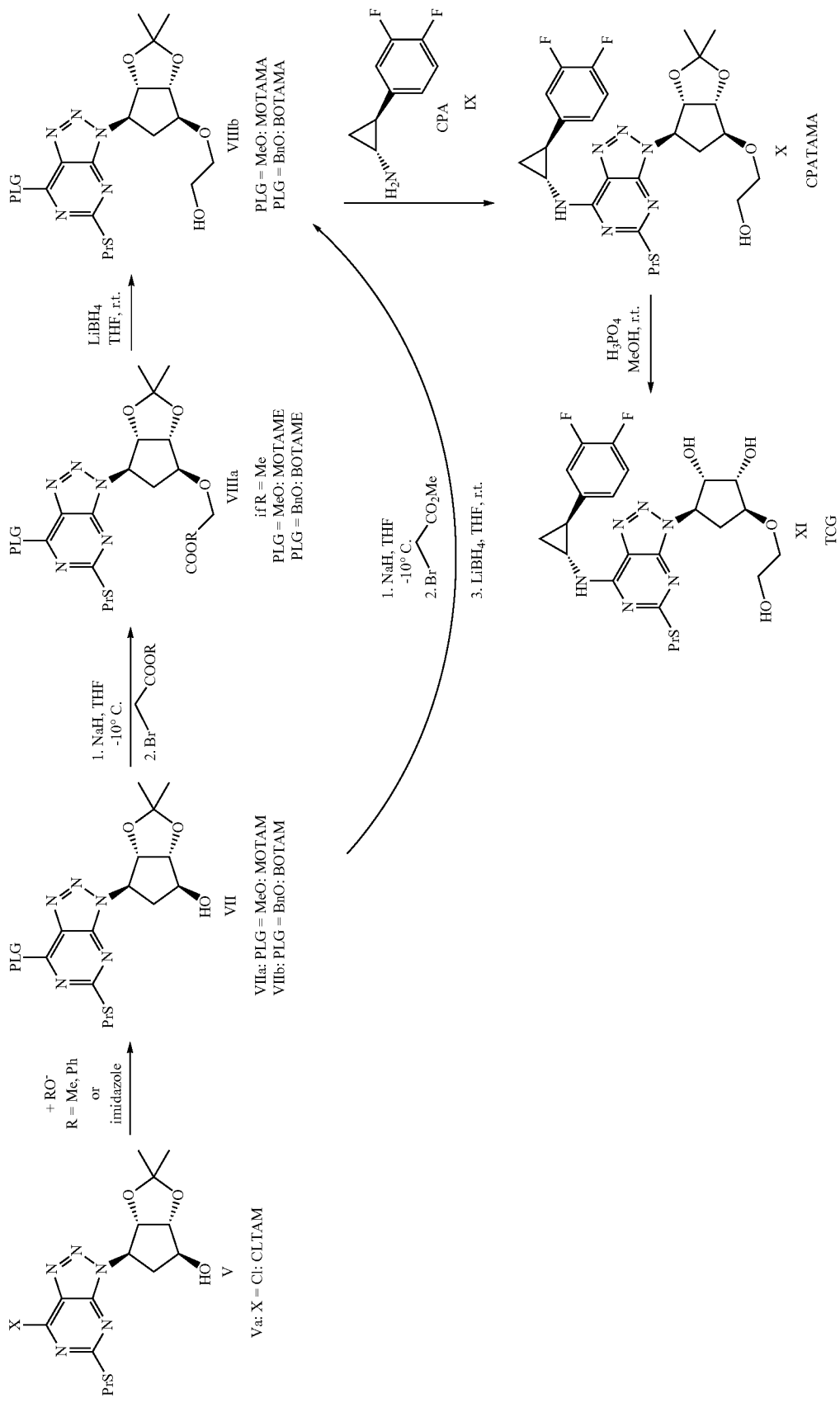

Alternatively, the compound of formula VII can be obtained by
(i) providing a compound of formula VI″

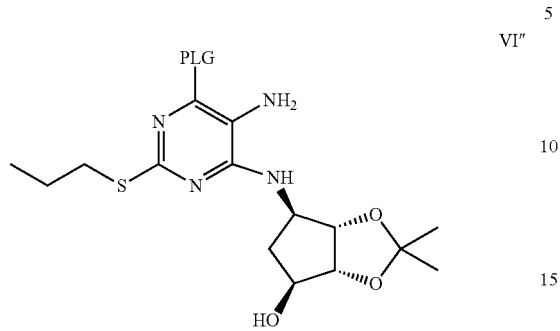

VI″ wherein PLG is defined as above, and
(ii) converting the compound of formula VI″ into the compound of formula VII by nitrosation.

The introduction of PLG can be applied in any of the steps of building-up the cyclopentyl substituted benzotriazole system as shown in a summary in Scheme 10. The nature of PLG determines in which particular step the introduction is the most convenient with respect to obtaining better yields. Introduction of PLG can be carried out in analogous reaction conditions as described above for the conversion of intermediate V to VII, optionally taking into consideration specialties of surrounding groups.

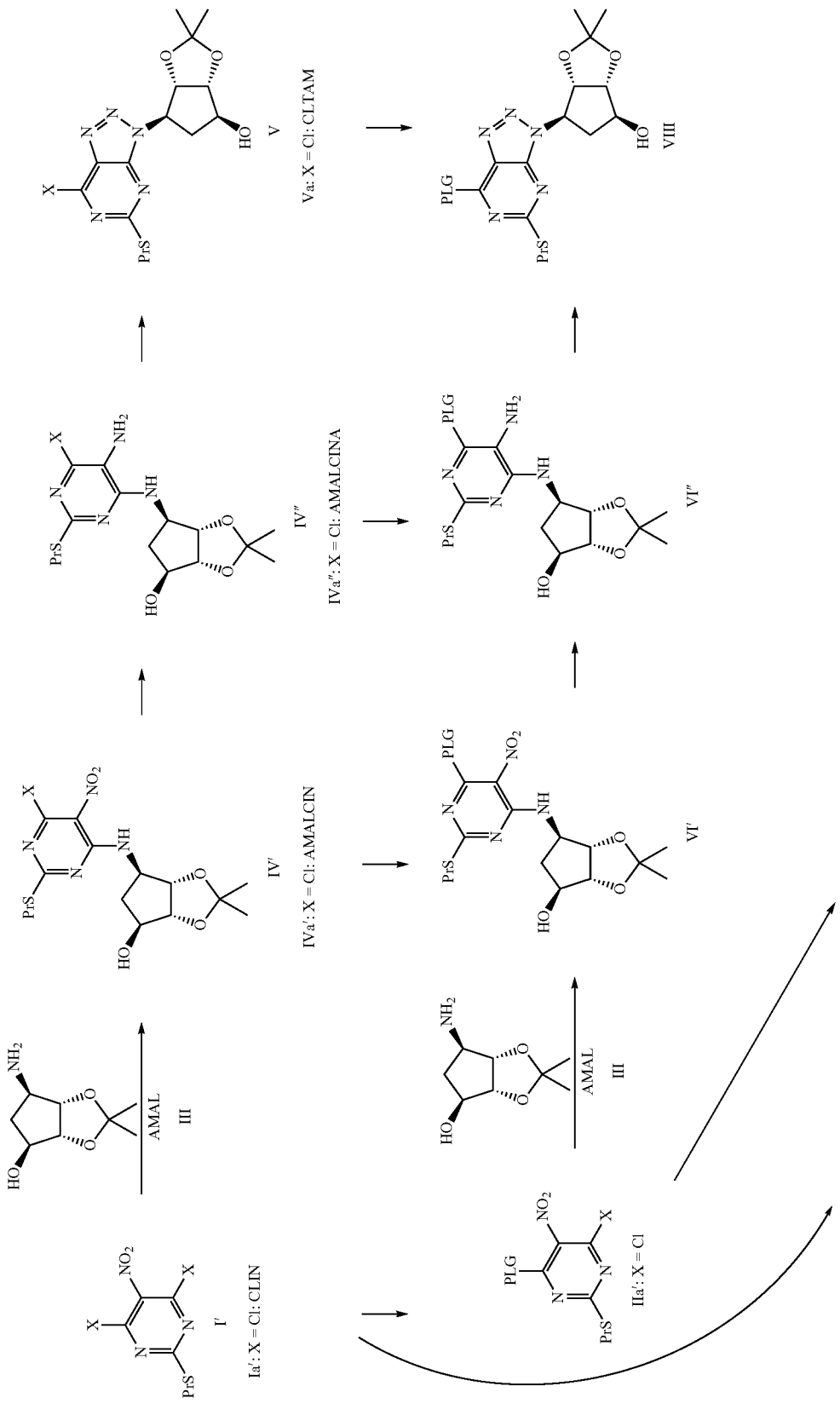
Scheme 10 is showing possible steps in which the PLG can be introduced in a process of building-up the cyclopentyl substituted benzotriazole.

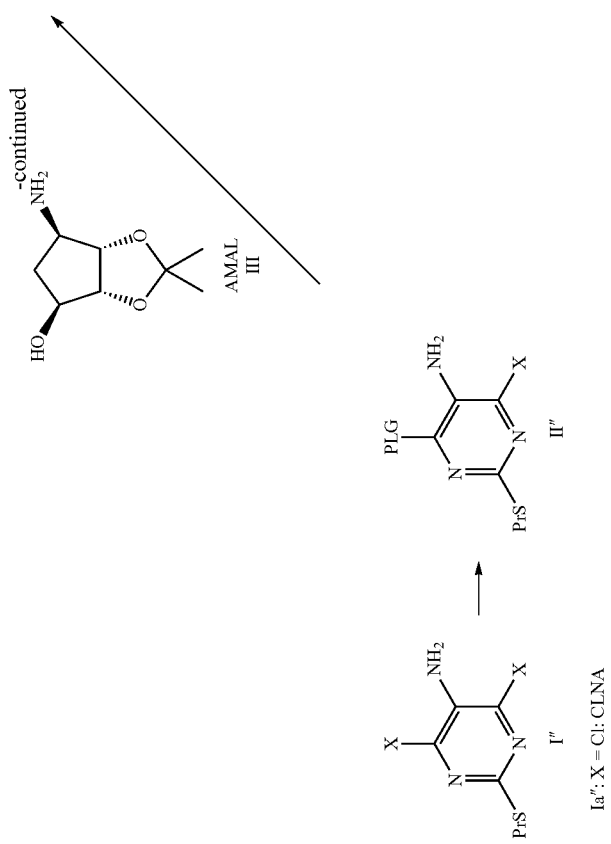

In another embodiment of the present invention the compound of formula VI" can be prepared by (0-1) providing a compound of formula IV"

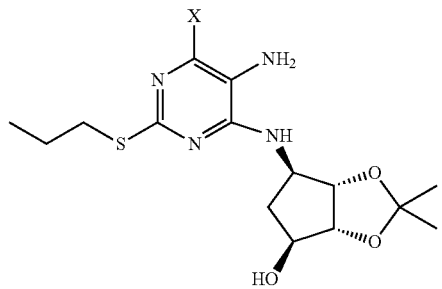

wherein X is Cl or Br, and (0-2) substituting X with PLG by reaction of a reagent PLG-H in the presence of a base, to obtain a compound of formula VI"

In such cases, the compound of formula IV" is obtained as described above.

Alternatively, the compound of formula VI" can be obtained by carrying out the reduction of the nitro group to amino group of the intermediate already comprising the PLG, by comprising the steps of:

(0-1') providing a compound of formula VI'

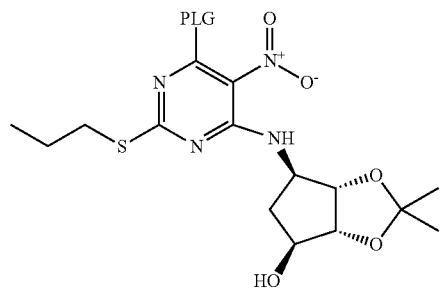

(0-2') reducing the nitro group of the compound of formula VI' to obtain a compound of formula VI"

The compound of formula VI' can be obtained from the compound of formula I'

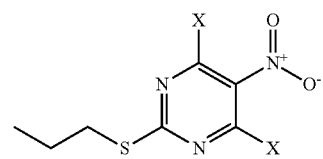

wherein X is Cl or Br, either by first reacting the compound of formula I' with the compound of formula III

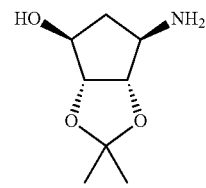

and subsequently substituting X with PLG by reaction of a reagent PLG-H in the presence of a base, or by first substituting X with PLG by reaction of a reagent PLG-H in the presence of a base, and subsequently reacting the obtained formula II' with the compound of formula III.

In yet another embodiment the compound of formula VI" can be prepared by (0-1") providing a compound of formula II"

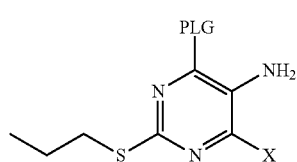

wherein X is Cl or Br, (0-2") reacting the compound of formula II" with a compound of formula III

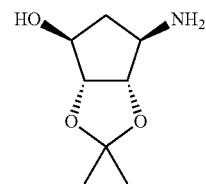

to obtain a compound of formula VI".

The compound of formula II" can be obtained from the compound of formula I'

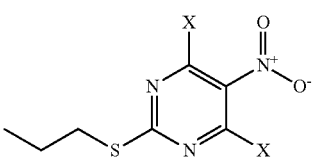

wherein X is Cl or Br, either by first reducing the nitro group of the compound of formula I' to obtain the compound of formula I", and subsequently substituting X with PLG by reaction of a reagent PLG-H in the presence of a base, or by first substituting X with PLG by reaction of a reagent PLG-H in the presence of a base, and subsequently reducing the nitro group of the compound of formula II'.

As set forth above, it is possible and corresponds to a particularly preferred embodiment of the present invention that several steps can be performed through one-pot conversions, without the need of isolation or separation of intermediate compounds. Accordingly, the possibility of reducing the number of required reaction steps, of increasing reaction selectivity, and of simplifying reactions respectively strongly contributes to provide an improved industrially applicable and economically beneficial process for obtaining triazolopyrimidine compounds and specifically ticagrelor. Thus, while of course separation or isolation of any of the intermediate compounds of formulae IV'''. VI' and VI'' can be carried out to obtain such compounds as useful intermediate compounds, this can be beneficially dispensed with if desired.

For example, methoxylation of heteroaryl halide, N-arylation of AMAL (III) and reduction of the nitro group can be carried in one-pot reaction simply by adding reagents and optionally an additional base or solvent.

In a characteristic part of the preferred embodiment, a conversion of CLINA (I'') to CLTAM (Va) can be carried out in one-pot by combining the step of N-arylation of AMAL (III) with the nitrosation step by adding excess of acetic acid simultaneously neutralising the present base and preparing the medium suitable for nitrosation.

In another embodiment, a compound of formula VII can be prepared by providing a compound of formula I'

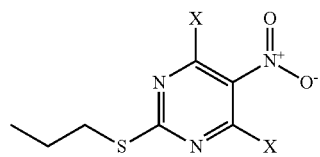

wherein X is Cl or Br,
substituting X with PLG by reaction of a reagent PLG-H in the presence of a base, to obtain a compound of formula II'

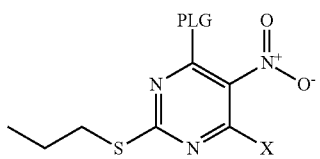

reacting the compound of formula II' with a compound of formula III

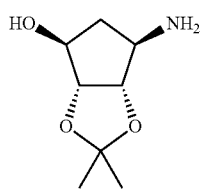

to obtain a compound of formula VI'

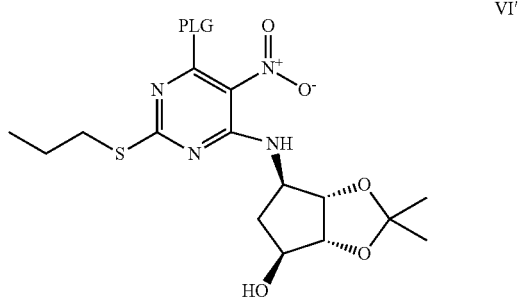

reducing the nitro group of the compound of formula VI' to obtain a compound of formula VI''

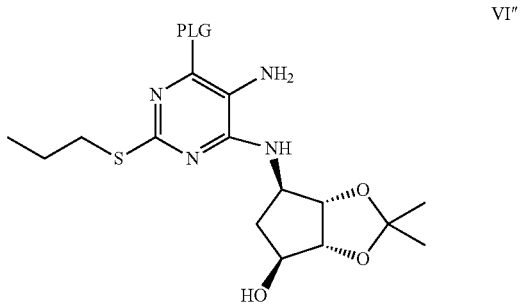

wherein PLG is defined as above, and
converting the compound of formula VI'' into the compound of formula VII by nitrosation, wherein all said steps are carried out in one pot.

In a characteristic part of the preferred embodiment, a one-pot process for the preparation of MOTAM (VIIa) from CLIN (I') is carried out. The PLG group is selected from alkoxy, preferably methoxy or benzyloxy. Methoxy substituted derivatives can be simply prepared in alkali metal methoxide solution in methanol, preferably in 1:1 molar methoxide/intermediate ratio. Reagents for other transformations can be taken from prior art approaches on heteroaryl halide analogues, such as iron in acetic acid for reduction of nitro group, reaction with AMAL in the presence of base such triethylamine or carbonate, nitrosation with organic nitrite in aprotic solvent or inorganic nitrite in acetic acid. The inertness of PLG enables the reduction of nitro group to be carried out in basic conditions using formamidinesulfinic acid (thiourea dioxide) or sodium dithionite, preferably formamidinesulfinic acid. Therefore, if basic conditions are used, the reduction of nitro group and subsequent nitrosation can be performed without isolating the intermediates, which represents a considerable shortening of the synthesis of substituted benzotriazoles.

A summary of the afore-mentioned one-pot processes is shown in the following scheme 11 below.

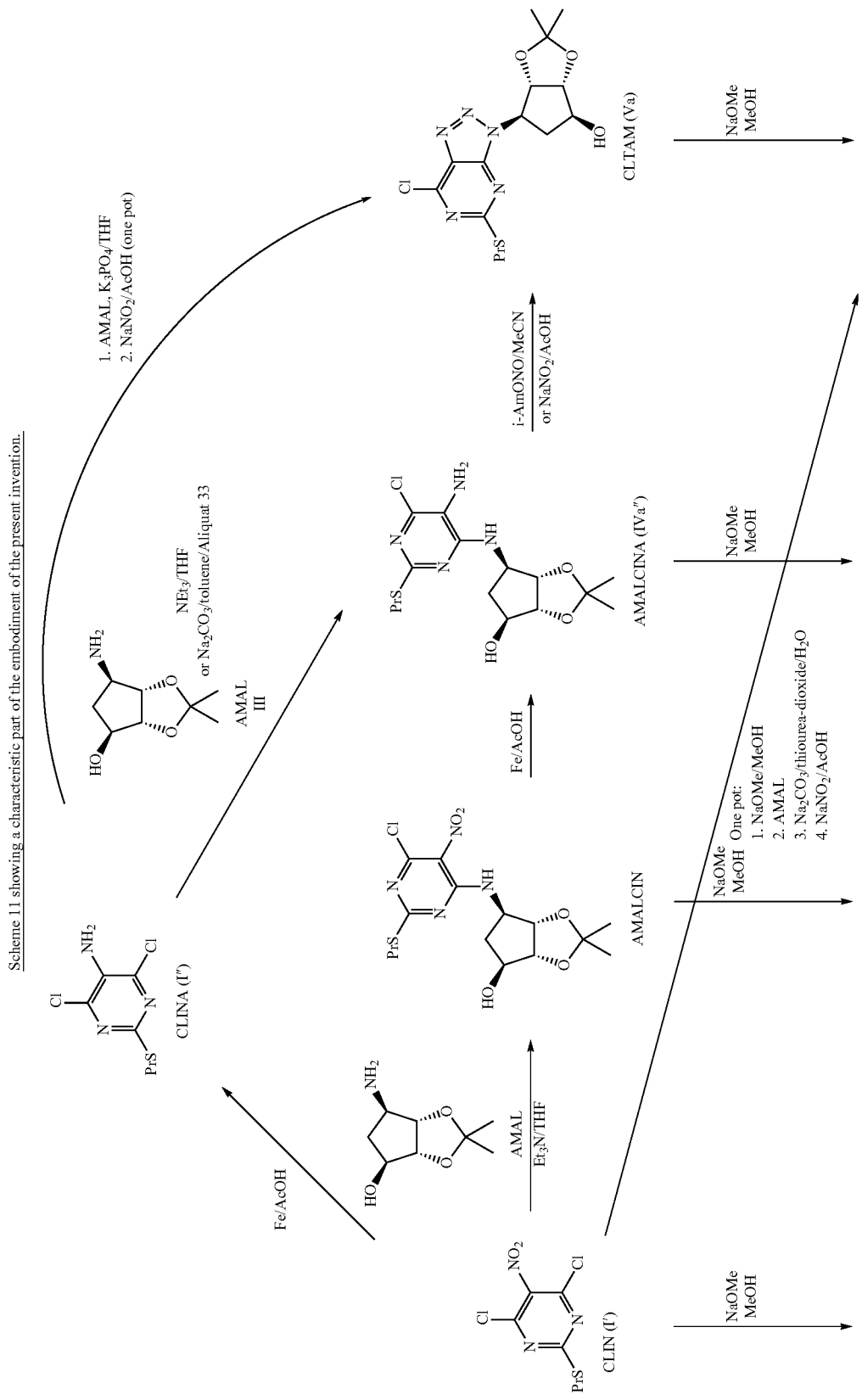

-continued
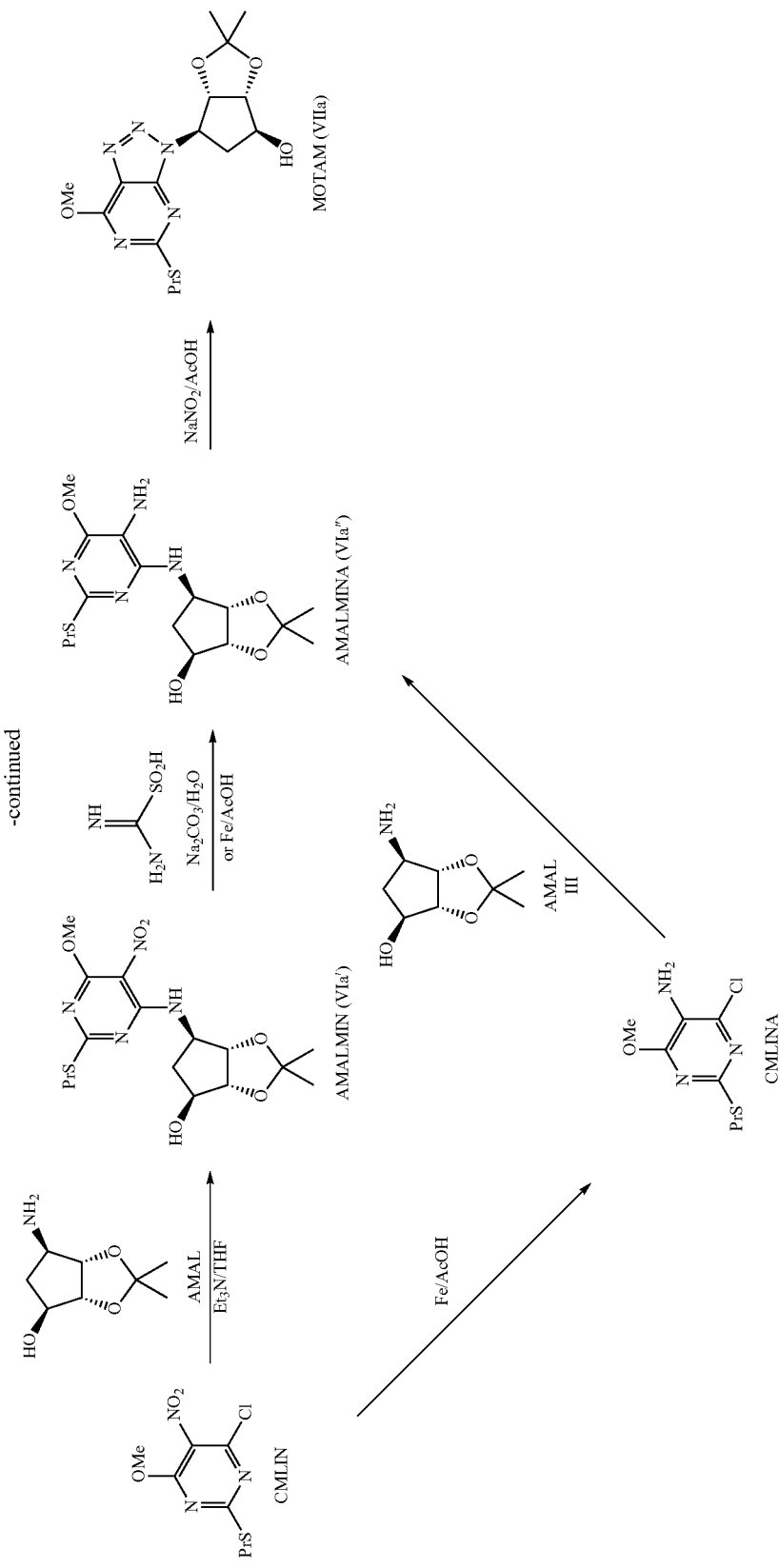

In another embodiment, the introduction of PLG group and the alkylation step can be joined using the same base and solvent (conversion of CLTAM (Va) to VIII). Furthermore, alkylation and reduction can be carried out in the same reaction mixture (conversion of VII to VIII"). For example in a special case the intermediate MOTAME (VIIIa') is not isolated but it can be further transferred to the reduction step. Using one-pot procedure as described in Scheme 11 and one-pot introduction of hydroxyethyl group reduces the overall procedure of the synthesis of ticagrelor to only four isolation steps starting from 4,6-dichloro-5-nitro-2-(propylthio)pyrimidine (CLIN=I').

In a further embodiment, the PLG group can be created indirectly from heteroaryl halides via more accessible intermediates as shown in Scheme 12. Some N-amidyl and N-imidyl groups can be prepared by alkylation and acylation of amino group.

Scheme 12 showing an embodiment of the present invention.

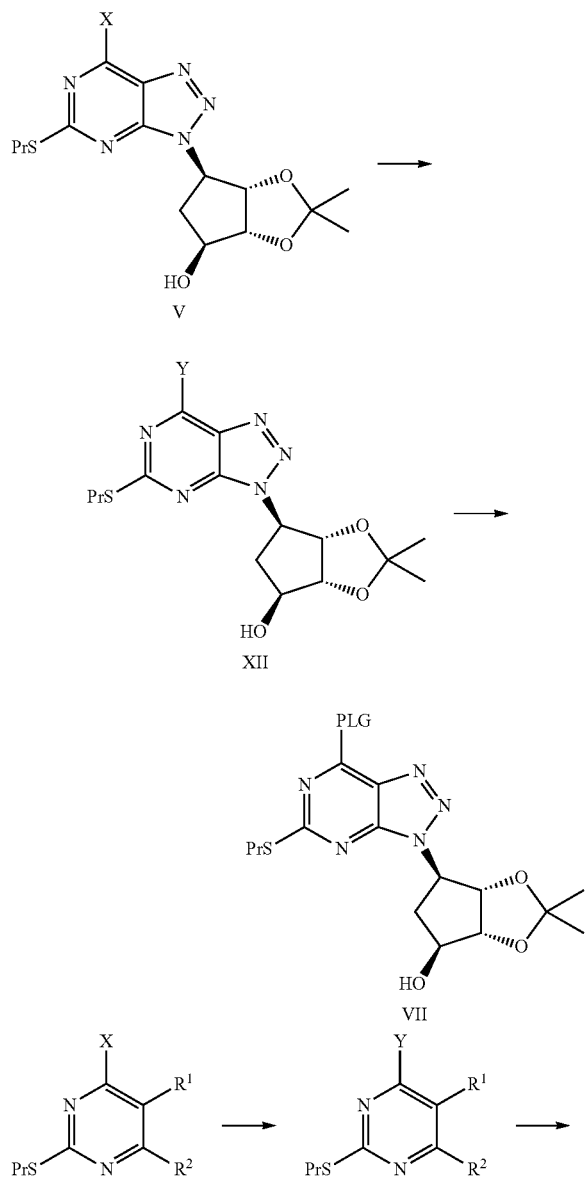
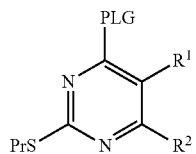
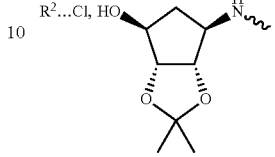

X...Cl, Br
R¹...NO₂, NH₂
R²...Cl, HO

Y...to PLG convertible group

In a further embodiment, the compound of formula VII is efficiently O-alkylated, preferably O-alkylated with halides or sulfonates of moieties which can be converted to 2-hydroxyethyl group.

Suitable reagents for such conversion are selected from haloacetic or sulfonyloxyacetic esters, preferably $C_1$-$C_4$-alkyl bromoacetates, most preferably methyl bromoacetate. Reaction of alkylation is performed in the presence of a strong base preferably sodium hydride to give intermediate VIII'. The ester functionality of compound VIII' is further reduced by use of hydrides, selected from aluminium or boron hydrides preferably from lithium aluminium hydride or alkali metal or zinc borohydride, most preferably from lithium borohydride.

The obtained compound of formula VIII" is transformed to the protected P2Y12 receptor antagonist preferably to propylidene derivative CPATAMA (X). Substitution of PLG group with amine side chain, preferably CPA (IX) is carried out either under net conditions (without solvent) or in a solvent, selected from non-nucleophilic solvents, preferably it is selected form nitriles, ethers, sulphoxides, sulfones, amides or a mixture thereof, more preferably from sulfoxides and amide solvents such as N-alkyl substituted acetamides, pyrrolidones and ureas, most preferably from dimethylsulfoxide and N,N-dimethylacetamide at temperatures from −20 to 100° C., most preferably at slightly elevated temperature from 25 to 70° C. Thus, despite lower reactivity of PLG, comparing to halogens substitution, the reaction surprisingly does not need harsh conditions. In the case of PLG being selected among the alkoxy groups derived from alcohols liquid at the reaction temperatures, these corresponding alcohols can also be efficiently used as solvents (e.g., methanol can be used when PLG is the methoxy group). In view of industrial application, the PLG should be carefully selected in order to obtain high yields in the amination reaction from the compound of formula VIII" to CPATAMA. When PLG is a linear or branched $C_1$-$C_6$-alkoxy group, optionally substituted with one or more aryl, heteroaryl, halo, $C_1$-$C_4$-alkoxy, or $C_1$-$C_4$-alkylthio, yields of amination reaction higher than 50% are obtained. Most preferably the PLG is methoxy or benzyloxy, which provides for yields of amination reaction higher than 70%. In addition, with higher yields, the level of impurities is lowered.

In a characteristic example of the embodiment, the methoxy intermediate MOTAME (VIII') is reduced by lithium borohydride to give MOTAMA (VIII"), which is further carried out to the nucleophilic aromatic substitution with cyclopropyl amine CPA (IX), where the methoxy group is in a role of a leaving group. Although in many heteroaryl systems methoxy group is not a satisfactory leaving group it was surprisingly found that the substitution in the triazolopyrimidine system performs smoothly with good yields. In opposite, the group is inert to oxy nucleophiles which can be formed during the alkylation step and no essential amounts of dimeric and polymeric side products were found when the reaction is conducted bellow −10° C.

In an alternative embodiment of the invention. PLG is substituted in the intermediate step of introduction of hydroxyethyl group. Thus, the intermediate VIII' is first treated with CPA (IX) in analogous conditions to those described for amination of compound VIII", to generate the intermediate XIII, which is further reduced to give CPA-TAMA (X). Both options are represented in Scheme 13.

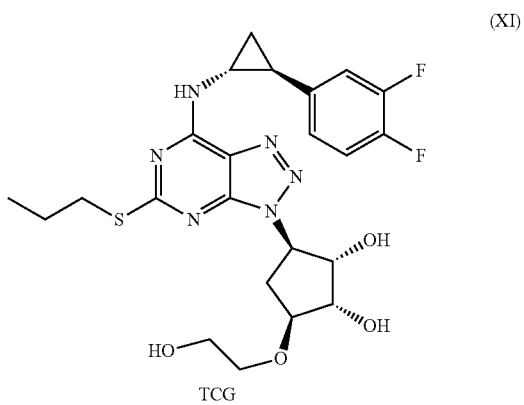 [SMILES: CCCSc1nc(N[C@@H]2C[C@H]2c2ccc(F)c(F)c2)c2nnn([C@@H]3C[C@H](OCCO)[C@@H](O)[C@H]3O)c2n1]

(XI)

TCG

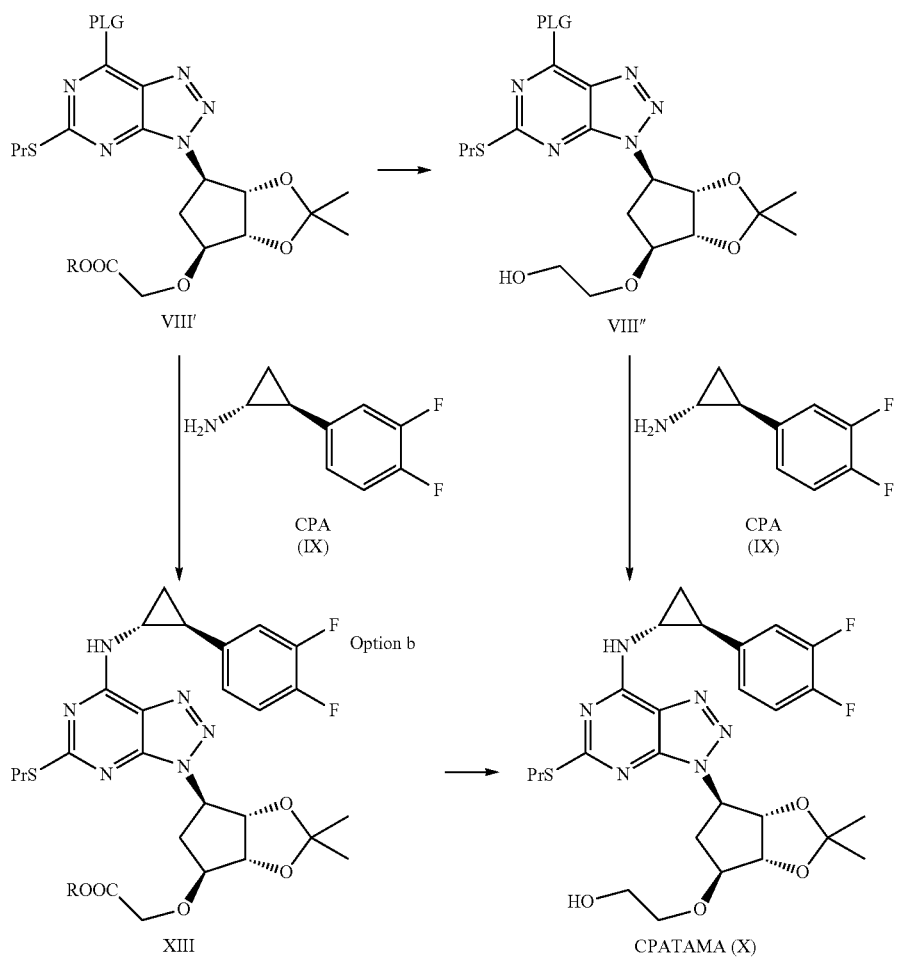

Scheme 13 showing an embodiment of the present invention.

Preparation of ticagrelor (TCG, XI) with the formula shown below follows prior art knowledge, wherein 2,2-propylidene protection group of glycolic part of cyclopentane is removed by using acids in protic solvents such as strong acids in alcohols or water or mixtures thereof, preferably hydrochloric or phosphoric acid in methanol or ethanol. If desired, a salt or a co-crystal of the compound of ticagrelor can be optionally prepared.

The ticagrelor compound prepared according to the invention may be used or administered on its own, preferably it is administered as a pharmaceutical composition comprising ticagrelor and a pharmaceutically acceptable excipient and/or carrier. Further, the ticagrelor compound prepared according to the invention may be combined with other drugs, especially drugs having activity against platelet aggregation or thrombolytic events.

In a further aspect of the present invention, a pharmaceutical composition comprising the compound of formula XI (ticagrelor, TCG), a salt or a co-crystal thereof is prepared by comprising the steps of preparing the compound of formula XI, a salt or a co-crystal thereof as described above, and mixing the compound of formula XI, a salt or a co-crystal thereof with a pharmaceutically acceptable carrier and/or excipient. The administration form can be suitably chosen, e.g. a form suitable for oral, parenteral, rectal administration and/or administration by inhalation, and the dosage form may be solid, liquid, or powdery. Therefore, the pharmaceutical composition comprising ticagrelor compound prepared according to the invention may suitably be in the form of tablets, pills, capsules, syrups, powders or granules for oral administration; or as sterile parenteral or subcutaneous solutions, suspensions for parenteral administration; or as suppositories for rectal administration.

Suitable excipients and/or carriers include, without being limited to, diluents, binders, disintegrants, lubricants, etc. For example, the compound or a finely divided form thereof, or particles comprising the compound, are mixed with a carrier or binder substance, e.g. a mono-, di- or polysaccharide such as sugars and starch, a sugar alcohol or another polyol. For example, lactose, saccharose, sorbitol, mannitol, starch, cellulose derivatives, a binder such as polyvinylpyrrolidone, and a lubricant such as magnesium stearate, calcium stearate, polyethylene glycol, waxes, paraffin, and the like are mixed, and than compressed into tablets. The compound or a finely divided form thereof or particles containing the same may be coated by another substance. The powder mixture or particles containing the compound may also be dispensed into capsules.

The pharmaceutical composition comprising ticagrelor prepared according to the invention in a desired dose is generally suitable to treat a disease or condition of a patient in need thereof, specifically to display a desired activity against platelet aggregation, or in the treatment or prophylaxis of thrombolytic events.

Further aspects of the present invention reside in the provision of valuable intermediate compounds II, VI and VIII useful in the synthesis of a compound of ticagrelor (TCG. XI), which intermediate compounds respectively have in common the protecting-leaving group PLG:

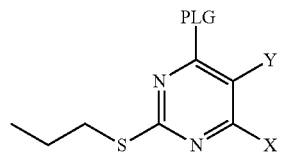

II wherein PLG is a protecting-leaving group. X is Cl or Br, and Y is $NO_2$ or $NH_2$,

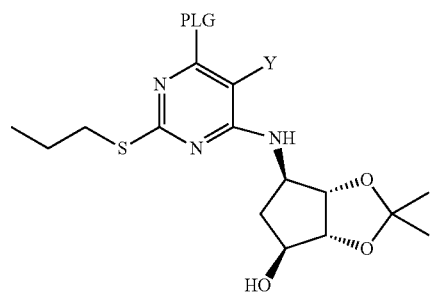

VI wherein PLG is a protecting-leaving group, and Y is $NO_2$ or $NH_2$,

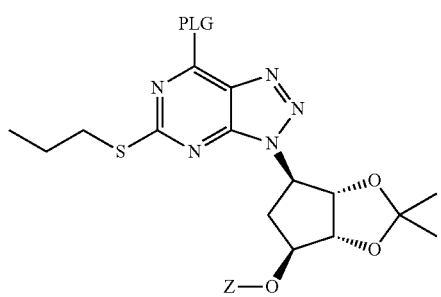

VIII wherein PLG is a protecting-leaving group, and Z is hydrogen, hydroxyethyl or a group convertible to hydroxyethyl.

As to the definition of "PLG" and "Z", reference is made to the descriptions elsewhere in the present specification.

Particular examples of such useful intermediate compounds are listed by their respective formulas below (in these formulas, "Pr" denotes "n-propyl"):

| Formula | Chemical name |
|---|---|
| ![structure] | 4-chloro-6-methoxy-5-nitro-2-(propylthio)pyrimidine |
| ![structure] | 4-chloro-6-methoxy-2-(propylthio)pyrimidin-5-amine |

| Formula | Chemical name |
|---|---|
| | (3aR,4S,6R,6aS)-6-((6-methoxy-5-nitro-2-(propylthio)pyrimidin-4-yl)amino)-2,2-dimethyltetrahydro-3aH-cyclopenta[d][1,3]dioxol-4-ol |
| | (3aR,4S,6R,6aS)-6-((5-amino-6-methoxy-2-(propylthio)pyrimidin-4-yl)amino)-2,2-dimethyltetrahydro-3aH-cyclopenta[d][1,3]dioxol-4-ol |
| | (3aR,4S,6R,6aS)-6-(7-Methoxy-5-(propylthio)-3H-[1,2,3]triazolo[4,5-d]pyrimidin-3-yl)-2,2-dimethyltetrahydro-3aH-cyclopenta[d][1,3]dioxol-4-ol |
| | Methyl 2-(((3aR,4S,6R,6aS)-6-(7-methoxy-5-(propylthio)-3H-[1,2,3]triazolo[4,5-d]pyrimidin-3-yl)-2,2-dimethyltetrahydro-3aH-cyclopenta[d][1,3]dioxol-4-yl)oxy)acetate |
| | Isopropyl 2-(((3aR,4S,6R,6aS)-6-(7-methoxy-5-(propylthio)-3H-[1,2,3]triazolo[4,5-d]pyrimidin-3-yl)-2,2-dimethyltetrahydro-3aH-cyclopenta[d][1,3]dioxol-4-yl)oxy)acetate |

| Formula | Chemical name |
|---|---|
| 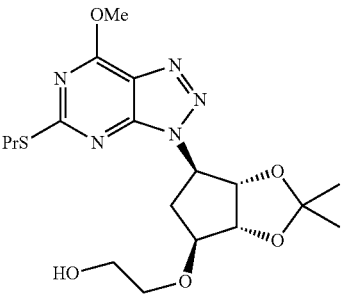 | 2-(((3aR,4S,6R,6aS)-6-(7-Methoxy-5-(propylthio)-3H-[1,2,3]triazolo[4,5-d]pyrimidin-3-yl)-2,2-dimethyltetrahydro-3aH-cyclopenta[d][1,3]dioxol-4-yl)oxy)ethanol |
| 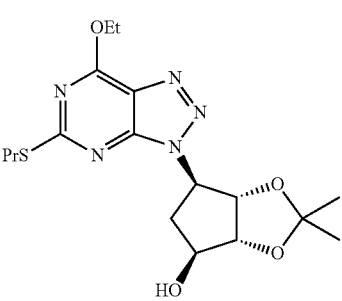 | (3aR,4S,6R,6aS)-6-(7-ethoxy-5-(propylthio)-3H-[1,2,3]triazolo[4,5-d]pyrimidin-3-yl)-2,2-dimethyltetrahydro-3aH-cyclopenta[d][1,3]dioxol-4-ol |
| 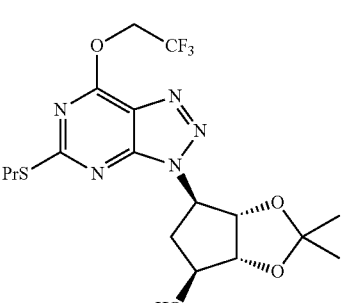 | (3aR,4S,6R,6aS)-2,2-dimethyl-6-(5-(propylthio)-7-(2,2,2-trifluoroethoxy)-3H-[1,2,3]triazolo[4,5-d]pyrimidin-3-yl)tetrahydro-3aH-cyclopenta[d][1,3]dioxol-4-ol |
| 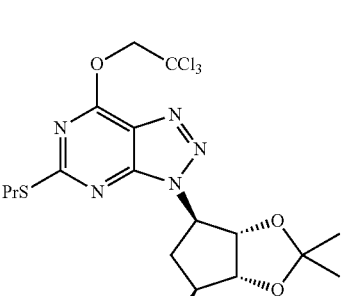 | (3aR,4S,6R,6aS)-2,2-dimethyl-6-(5-(propylthio)-7-(2,2,2-trichloroethoxy)-3H-[1,2,3]triazolo[4,5-d]pyrimidin-3-yl)tetrahydro-3aH-cyclopenta[d][1,3]dioxol-4-ol |
| 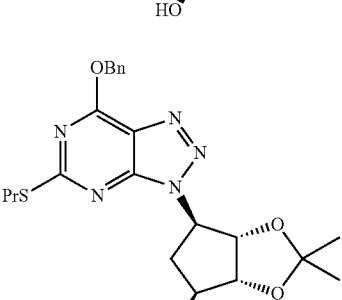 | (3aR,4S,6R,6aS)-6-(7-(benzyloxy)-5-(propylthio)-3H-[1,2,3]triazolo[4,5-d]pyrimidin-3-yl)-2,2-dimethyltetrahydro-3aH-cyclopenta[d][1,3]dioxol-4-ol |

| Formula | Chemical name |
|---|---|
|  | methyl 2-(((3aR,4S,6R,6aS)-6-(7-(benzyloxy)-5-(propylthio)-3H-[1,2,3]triazolo[4,5-d]pyrimidin-3-yl)-2,2-dimethyltetrahydro-3aH-cyclopenta[d][1,3]dioxol-4-yl)oxy)acetate |
|  | 2-(((3aR,4S,6R,6aS)-6-(7-(benzyloxy)-5-(propylthio)-3H-[1,2,3]triazolo[4,5-d]pyrimidin-3-yl)-2,2-dimethyltetrahydro-3aH-cyclopenta[d][1,3]dioxol-4-yl)oxy)ethanol |
|  | (3aR,4S,6R,6aS)-2,2-Dimethyl-6-(7-phenoxy-5-(propylthio)-3H-[1,2,3]triazolo[4,5-d]pyrimidin-3-yl)tetrahydro-3aH-cyclopenta[d][1,3]dioxol-4-ol |
|  | (3aR,4S,6R,6aS)-6-(7-(4-methoxyphenoxy)-5-(propylthio)-3H-[1,2,3]triazolo[4,5-d]pyrimidin-3-yl)-2,2-dimethyltetrahydro-3aH-cyclopenta[d][1,3]dioxol-4-ol |

| Formula | Chemical name |
|---|---|
| 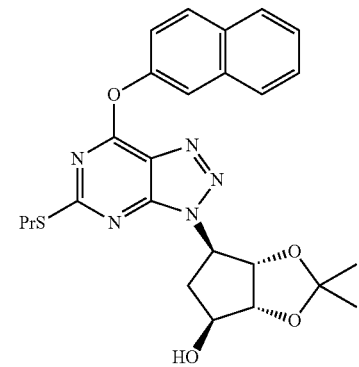 | (3aR,4S,6R,6aS)-2,2-dimethyl-6-(7-(naphthalen-2-yloxy)-5-(propylthio)-3H-[1,2,3]triazolo[4,5-d]pyrimidin-3-yl)tetrahydro-3aH-cyclopenta[d][1,3]dioxol-4-ol |
| 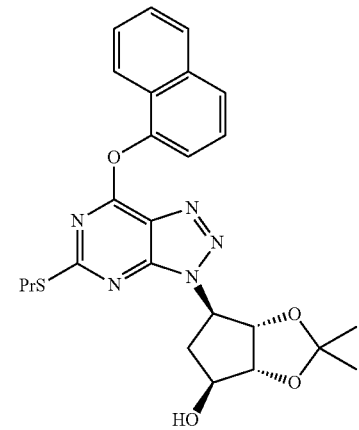 | (3aR,4S,6R,6aS)-2,2-dimethyl-6-(7-(naphthalen-1-yloxy)-5-(propylthio)-3H-[1,2,3]triazolo[4,5-d]pyrimidin-3-yl)tetrahydro-3aH-cyclopenta[d][1,3]dioxol-4-ol |
| 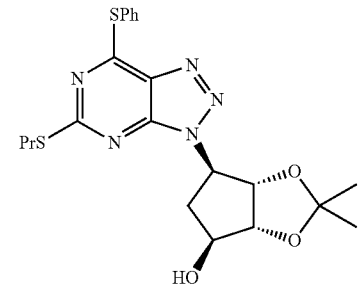 | (3aR,4S,6R,6aS)-2,2-dimethyl-6-(7-(phenylthio)-5-(propylthio)-3H-[1,2,3]triazolo[4,5-d]pyrimidin-3-yl)tetrahydro-3aH-cyclopenta[d][1,3]dioxol-4-ol |
| 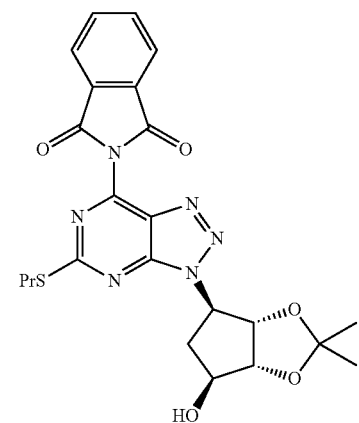 | 2-(3-((3aS,4R,6S,6aR)-6-hydroxy-2,2-dimethyltetrahydro-3aH-cyclopenta[d][1,3]dioxol-4-yl)-5-(propylthio)-3H-[1,2,3]triazolo[4,5-d]pyrimidin-7-yl)isoindoline-1,3-dione |

| Formula | Chemical name |
|---|---|
| | (3aR,4S,6R,6aS)-6-(7-(1H-Imidazol-1-yl)-5-(propylthio)-3H-[1,2,3]triazolo[4,5-d]pyrimidin-3-yl)-2,2-dimethyltetrahydro-3aH-cyclopenta[d][1,3]dioxol-4-ol |

In the following the present invention will be described in further detail by illustrative, non-limiting examples.

EXPERIMENTAL PROCEDURES

Example 1

Preparation of 4,6-dichloro-2-(propylthio)pyrimidin-5-amine (CLINA)

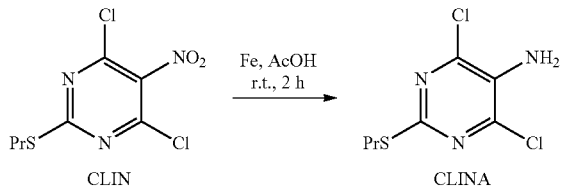

To a mixture of Fe (167 g, 3 mol) in AcOH (1 L) 4,6-dichloro-5-nitro-2-(propylthio)pyrimidine (CLIN, 100 g, 0.37 mol) was slowly added over 2 h, and reaction mixture was then stirred at room temperature for additional 2 h. Salts were then filtered off and the filtrate concentrated. EtOAc was added (400 mL), organic layer was washed with water (3×200 mL), dried over MgSO$_4$, and concentrated to afford oily product (65.2 g, 73% yield). $^1$H NMR (CDCl$_3$, 500 MHz) δ 1.03 (t, J=7.4 Hz, 3H), 1.73 (m, 2H), 3.07 (m, 2H), 4.23 (br s, 2H); MS (ESI) m/z: 238 [MH]$^+$.

Example 2

Preparation of (3aR,4S,6R,6aS)-6-((6-chloro-5-nitro-2-(propylthio)pyrimidin-4-yl)amino)-2,2-dimethyltetrahydro-3aH-cyclopenta[d][1,3]dioxol-4-ol (AMALCIN)

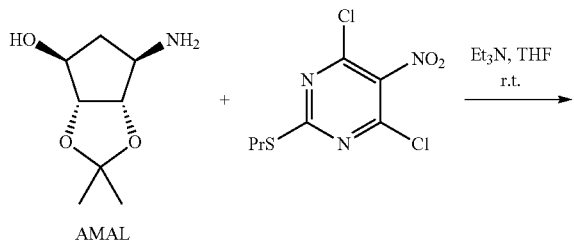

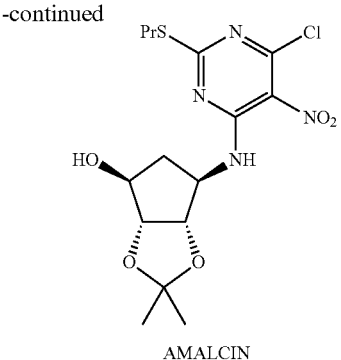

The title compound was prepared using the method described in WO 00/34283.

To a solution of CLIN (11.6 g, 43.3 mmol) and Et$_3$N (4.0 mL, 28.9 mmol) in dry THF (100 mL) solution of AMAL (5.0 g, 28.9 mmol) in dry THF (100 mL) was slowly added at room temperature, and resulting reaction mixture was stirred for 1 h. Salts were filtered off, washed with dry THF (50 mL), filtrate was concentrated, and crude product was purified by crystallization from hexane/EtOAc mixture to afford yellowish powder (m=9.88 g, 84% yield). MP 63° C.; $^1$H NMR (DMSO-d$_6$, 500 MHz) δ 0.98 (t, J=7.3 Hz, 3H), 1.19 (s, 3H), 1.34 (s, 3H), 1.64-1.78 (m, 3H), 2.17 (m, 1H), 3.04 (m, 1H), 3.12 (m, 1H), 4.11 (m, 1H), 4.44 (m, 1H), 4.53-4.58 (m, 2H), 8.76 (br d, J=7.9 Hz, 1H); MS (ESI) m/z: 405 [MH]$^+$.

Example 3

Preparation of (3aR,4S,6R,6aS)-6-((5-amino-6-chloro-2-(propylthio)pyrimidin-4-yl)amino)-2,2-dimethyltetrahydro-3aH-cyclopenta[d][1,3]dioxol-4-ol (AMALCINA)

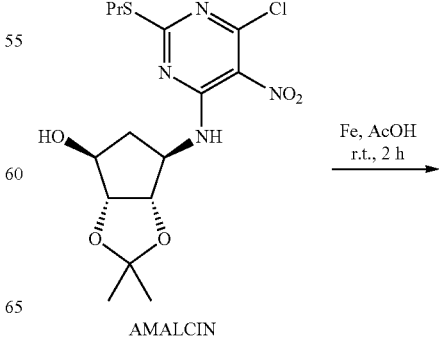

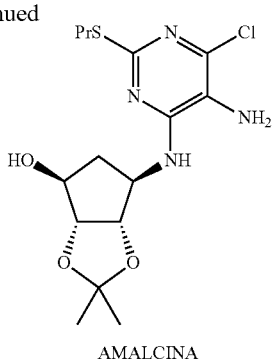

AMALCINA

The title compound was prepared using the method described in WO 00/34283.

A solution of AMALCIN (0.50 g, 1.23 mmol) was slowly added to a stirring mixture of AcOH (3 mL) and Fe (0.84 g, 15.0 mmol). Resulting reaction mixture was stirred at room temperature for 2 h. Then salts were filtered off, and AcOH evaporated. Water was added (20 mL), and product was extracted to EtOAc (3×10 mL). Combined organic layers were washed with saturated $Na_2CO_3$ (3×10 mL), dried over $MgSO_4$, and concentrated to afford title compound as brown syrup (m=0.44 g, 96% yield). $^1$H NMR (CDCl$_3$, 500 MHz) δ 0.96 (t, J=7.3 Hz, 3H), 1.18 (s, 3H), 1.37 (s, 3H), 1.68 (m, 2H), 1.78 (m, 1H), 2.27 (m, 1H), 2.94 (m, 1H), 3.08 (m, 1H), 3.30 (br s, 2H), 4.34 (m, 1H), 4.46-4.55 (m, 4H), 6.12 (br d, J=8.3 Hz, 1H); MS (ESI) m/z: 375 [MH]$^+$.

AMALCINA was also prepared from AMAL and CLINA.

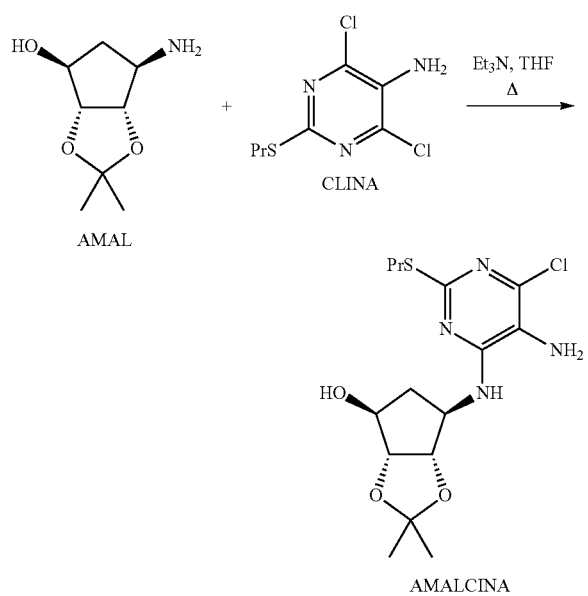

To a solution of AMAL (7.64 g, 44.1 mmol) and CLINA (10.5 g, 44.1 mmol) in dry THF (40 mL) Et$_3$N (6.76 mL, 48.5 mmol) was added at room temperature. Resulting reaction mixture was stirred at reflux for 24 h, then salts were filtered off, and solvent evaporated to afford crude product, which was then purified by chromatography (SiO$_2$, hexane:EtOAc). Brown syrup (14.4 g, 87% yield).

Or:

To a solution of AMAL (1.45 g, 8.40 mmol) and CLINA (2.0 g, 8.40 mmol) in toluene (20 mL) Na$_2$CO$_3$ (1.07 g, 10.1 mmol) and Aliquat 336 (0.34 g, 0.84 mmol) were added at room temperature. Resulting reaction mixture was stirred at 100° C. for 48 h, then salts were filtered off, and solvent evaporated to afford crude product, which was then purified by chromatography (SiO$_2$, hexane:EtOAc). Brown syrup (2.52 g, 80% yield).

Example 4

Preparation of (3aR,4S,6R,6aS)-6-(7-chloro-5-(propylthio)-3H-[1,2,3]triazolo[4,5-d]pyrimidin-3-yl)-2,2-dimethyltetrahydro-3aH-cyclopenta[d][1,3]dioxol-4-ol (CLTAM)

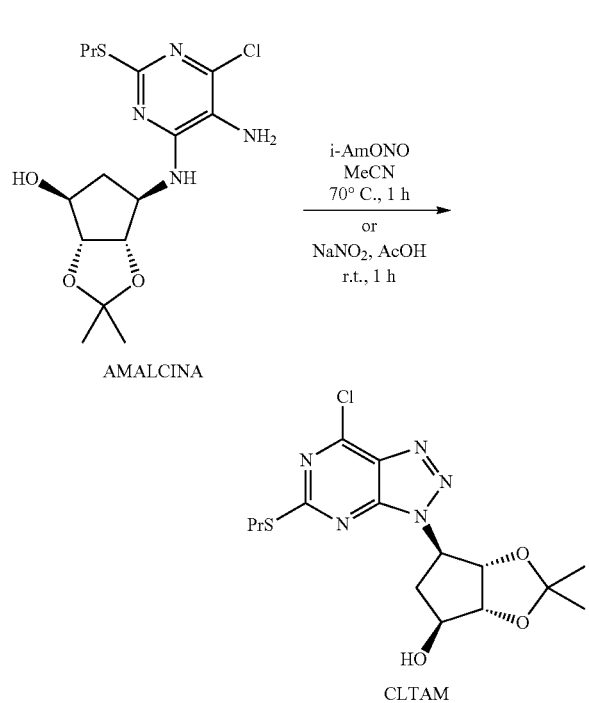

The title compound was prepared according the method described in WO 00/34283.

A solution of AMALCINA (6.0 g, 16.0 mmol) and i-AmONO (3.23 mL, 24.0 mmol) in dry MeCN (100 mL) was stirred at 70° C. for 1 h, then solvent was evaporated to afford crude product, which was then purified by chromatography (SiO$_2$, hexane:EtOAc). Slightly yellowish oil which crystallized upon standing. (5.70 g, 92% yield). Mp 83° C.; $^1$H NMR (CDCl$_3$, 500 MHz) δ 1.09 (t, J=7.4 Hz, 3H), 1.32 (s, 3H), 1.53 (s, 3H), 1.82 (m, 2H), 2.39 (m, 1H), 2.88 (m, 1H), 3.22 (m, 2H), 3.78 (d, J=8.4 Hz, 1H), 4.43 (m, 1H), 4.78 (m, 1H), 5.07 (m, 1H), 5.32 (m, 1H); MS (ESI) m/z: 386 [MH]$^+$.

The title compound was also prepared using the method described in WO 01/92263.

To a solution of AMALCINA (1.0 g, 2.67 mmol) in AcOH (5 mL) at room temperature NaNO$_2$ (0.20 g, 2.64 mmol) was slowly added. Resulting reaction mixture was stirred at room temperature for 1 h, then AcOH was evaporated, water (50 mL) was added, and product was extracted to MeTHF (3×10 mL). Combined organic phases were washed with saturated Na$_2$CO$_3$ (3×10 mL), dried over MgSO$_4$, and concentrated to afford crude product, which was then crystallized from hexane/EtOAc mixture. White powder (0.95 g, 92% yield).

CLTAM was also prepared through one-pot reaction starting from AMAL and CLINA.

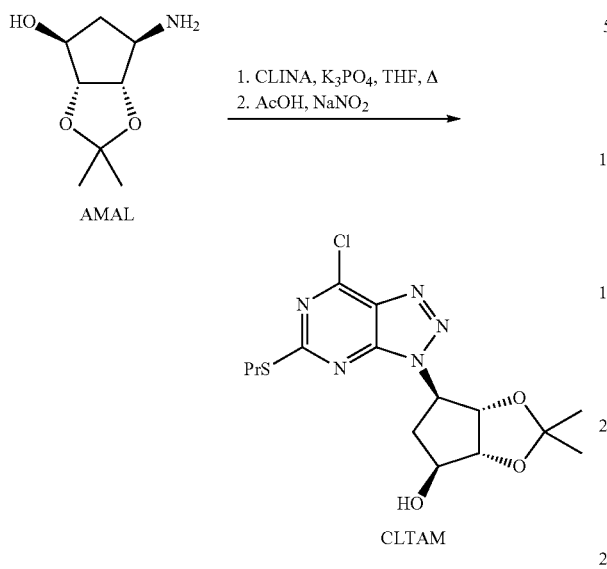

To a solution of AMAL (7.64 g, 44.1 mmol) and CLINA (10.5 g, 44.1 mmol) in dry THF (40 mL) K$_3$PO$_4$ (10.3 g, 48.5 mmol) was added at room temperature. Resulting reaction mixture was stirred at reflux for 24 h, then AcOH was slowly added (100 mL) followed by NaNO$_2$ (3.65 g, 52.9 mmol). Reaction mixture was stirred at room temperature for 1 h, then solvents were evaporated, water (100 mL) was added, and product was extracted to MeTHF (3×50 mL). Combined organic phases were washed with saturated NaHCO$_3$ (3×50 mL), dried over MgSO$_4$, and concentrated to afford crude product, which was then purified by chromatography (SiO$_2$, hexane:EtOAc) to afford colorless crystals (12.2 g, 72% yield).

Example 5

Preparation of 4-chloro-6-methoxy-5-nitro-2-(propylthio)pyrimidine (CMLIN)

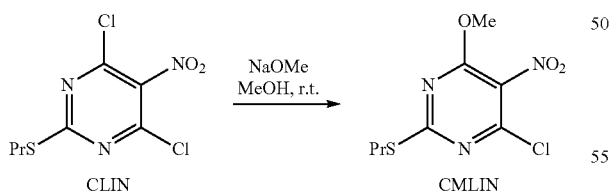

To a solution of CLIN (1.0 g, 3.73 mmol) in dry MeOH (10 mL) NaOMe (0.20 g, 3.73 mmol) was slowly added, and reaction mixture was then stirred at room temperature for 1 h. AcOH (1 mL) and water (20 mL) were added, and product was extracted to MeTHF (3×10 mL). Combined organic phases were dried over MgSO$_4$ and concentrated to afford crude product, which was then purified by chromatography (SiO$_2$, hexane:EtOAc) to afford yellow oil (0.78 g, 79% yield). MS (ESI) m/z: 264 [MH]$^+$.

Example 6

Preparation of 4-chloro-6-methoxy-2-(propylthio)pyrimidin-5-amine (CMLINA)

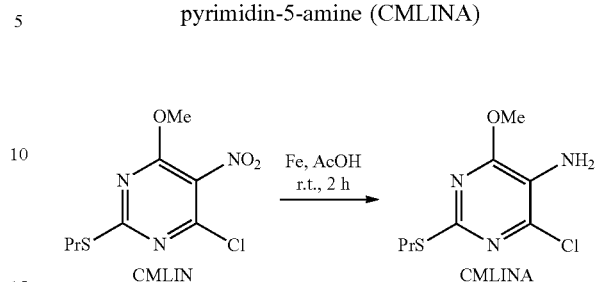

To a solution of CMLIN (0.10 g, 0.57 mmol) in AcOH (2 mL) Fe (98 mg, 1.75 mmol) was added, and reaction mixture was then stirred at room temperature for 2 h. Salts were then filtered off and filtrate concentrated. EtOAc was added (400 mL), organic layer was washed with water (3×200 mL), dried over MgSO$_4$, and concentrated to afford oily product (0.60 g, 68% yield). MS (ESI) m/z: 234 [MH]$^+$.

Example 7

Preparation of (3aR,4S,6R,6aS)-6-((6-methoxy-5-nitro-2-(propylthio)pyrimidin-4-yl)amino)-2,2-dimethyltetrahydro-3aH-cyclopenta[d][1,3]dioxol-4-ol (AMALMIN)

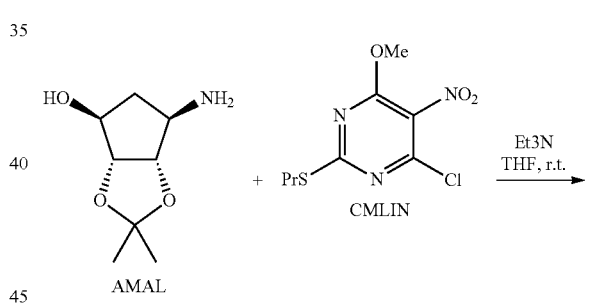

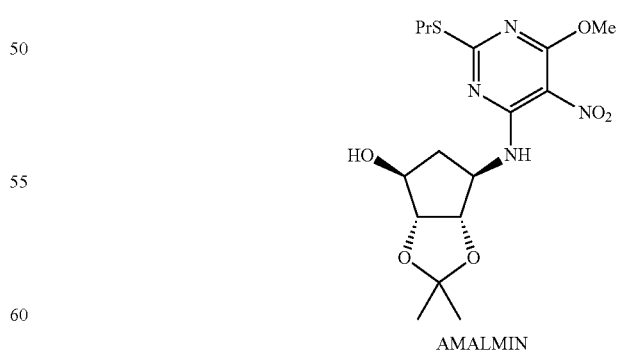

To a solution of CMLIN (0.15 g, 0.57 mmol) and Et$_3$N (87 L, 0.63 mmol) in dry THF (2 mL) AMAL (0.10 g, 0.57 mmol) was slowly added, and reaction mixture was then stirred at room temperature for 1 h. Salts were filtered off and filtrate was concentrated to afford yellow oil (0.22 g, 96% yield). MS (ESI) m/z: 401 [MH]⁺.

AMALMIN was also prepared from AMALCIN.

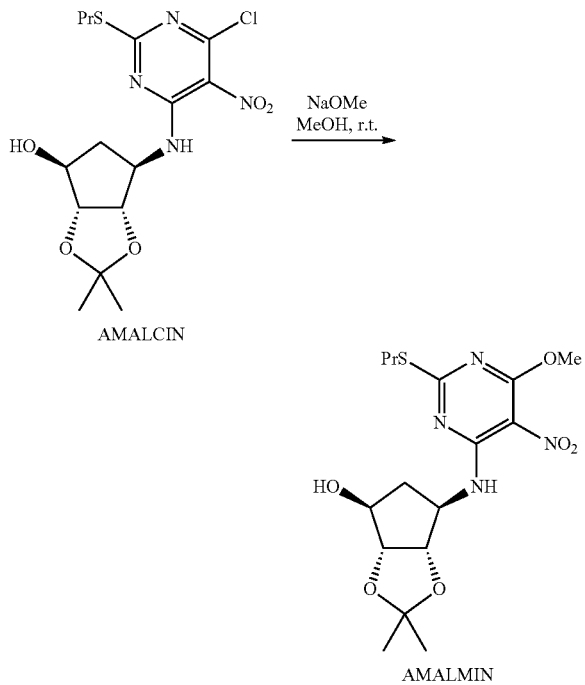

To a solution of AMALCIN (1.78 g, 4.40 mmol) in dry MeOH (10 mL) NaOMe (0.25 g, 4.62 mmol) was slowly added, and reaction mixture was then stirred at room temperature for 1 h. AcOH (1 mL) and water (50 mL) were added, and product was extracted to CH$_2$Cl$_2$ (3×20 mL). Combined organic phases were dried over MgSO$_4$ and concentrated to afford crude product, which was then purified by chromatography (SiO$_2$, hexane:EtOAc) to afford yellowish powder (1.49 g, 85% yield).

Example 8

Preparation of (3aR,4S,6R,6aS)-6-((5-amino-6-methoxy-2-(propylthio)pyrimidin-4-yl)amino)-2,2-dimethyltetrahydro-3aH-cyclopenta[d][1,3]dioxol-4-ol (AMALMINA)

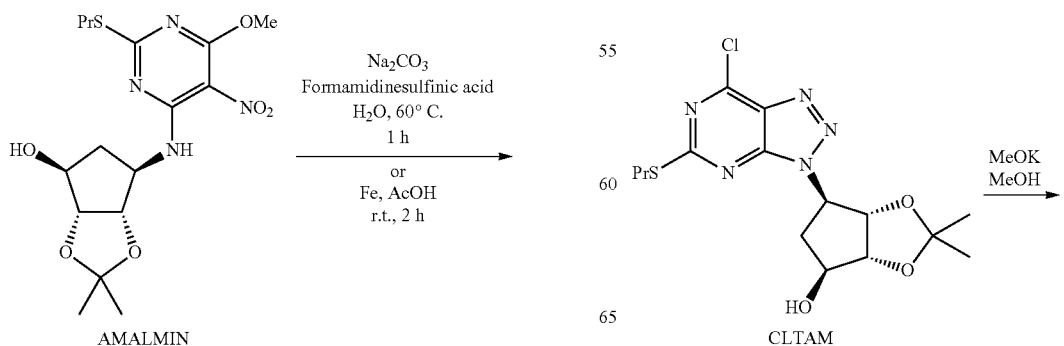

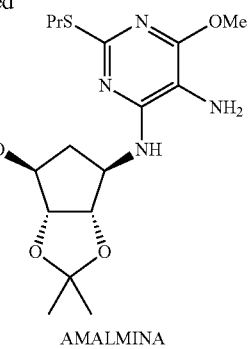

AMALMINA

A mixture of AMALMIN (0.40 g, 1.0 mmol), Na$_2$CO$_3$ (0.35 g, 3.3 mmol) and formamidinesulfinic acid (0.36 g, 3.3 mmol) in MeOH (5 mL) and water (0.5 mL) was stirred at 60° C. for 1 h. Then water was added (20 mL), and product was extracted to MeTHF (3×10 mL). Combined organic layers were dried over MgSO$_4$, and concentrated to afford crude product, which was then purified by chromatography (SiO$_2$, hexane:EtOAc) to give AMALMINA as brown oil (m=0.31 g, 85% yield). MS (ESI) m/z: 371 [MH]⁺.

The title compound was prepared using the method described in WO 00/34283.

A solution of AMALMIN (1.0 g, 2.50 mmol) was slowly added to a stirring mixture of AcOH (20 mL) and Fe (1.40 g, 25.0 mmol). Resulting reaction mixture was stirred at room temperature for 2 h. Then salts were filtered off, and AcOH evaporated. Water was added (20 mL), and product was extracted to MeTHF (3×10 mL). Combined organic layers were washed with saturated Na$_2$CO$_3$ (3×10 mL), dried over MgSO$_4$, and concentrated to afford title compound as brown syrup (m=0.74 g, 80% yield).

Example 9

Preparation of (3aR,4S,6R,6aS)-6-(7-methoxy-5-(propylthio)-3H-[1,2,3]triazolo[4,5-d]pyrimidin-3-yl)-2,2-dimethyltetrahydro-3aH-cyclopenta[d][1,3]dioxol-4-ol (MOTAM)

-continued

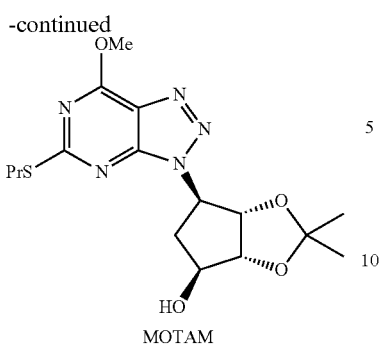

MOTAM

To a solution of CLTAM (0.50 g, 1.30 mmol) in dry MeOH (2 mL) at room temperature 25% solution of KOMe in MeOH (0.42 mL, 1.43 mmol) was added, and resulting reaction mixture was stirred for 15 min. Water was added (10 mL), and product was extracted to MeTHF (3×5 mL). Combined organic layers were dried over MgSO$_4$, and concentrated to afford title compound as brownish syrup (m=0.45 g, 90% yield). $^1$H NMR (CDCl$_3$, 500 MHz) δ 1.05 (t, J=7.3 Hz, 3H), 1.28 (s, 3H), 1.49 (s, 3H), 1.79 (m, 2H), 2.29 (m, 1H), 2.85 (m, 1H), 2.56 (m, 1H), 3.17 (m, 2H), 4.20 (s, 3H), 4.38 (br d, J=5.2 Hz, 1H), 4.46 (br s, 1H), 4.76 (m, 1H), 4.95 (m, 1H), 5.30 (m, 1H); MS (ESI) m/z: 382 [MH]$^+$.

MOTAM was also prepared from CLTAM using K$_2$CO$_3$/MeOH.

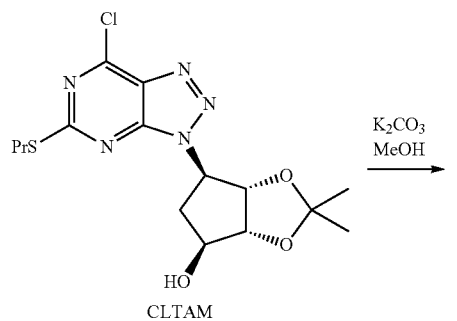

CLTAM $\xrightarrow{\text{K}_2\text{CO}_3}{\text{MeOH}}$

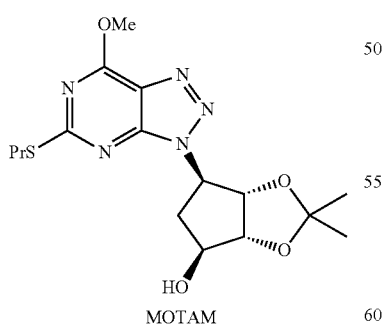

MOTAM

To a solution of CLTAM (10.0 g, 25.9 mmol) in dry MeOH (50 mL) at room temperature K$_2$CO$_3$ (3.94 g, 28.5 mmol) was added, and resulting reaction mixture was stirred for 2 h. Solvent was evaporated, MeTHF (100 mL) was added, and salts were filtered off. Organic phase was washed with brine (3×100 mL) and water (2×100 mL), dried over MgSO$_4$, and concentrated to afford title compound as yellowish syrup (m=9.39 g, 95% yield).

MOTAM was also prepared from AMALMINA.

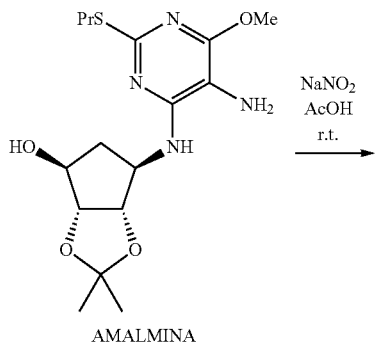

$\xrightarrow[\text{r.t.}]{\text{NaNO}_2 \text{ AcOH}}$

AMALMINA

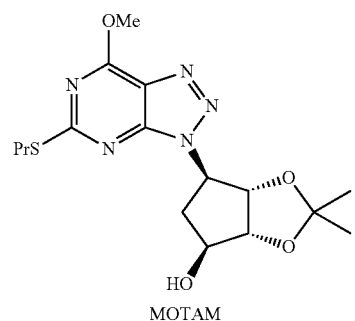

MOTAM

To a solution of AMALMINA (0.5 g, 1.35 mmol) in AcOH (5 mL) at room temperature NaNO$_2$ (0.10 g, 1.48 mmol) was added. Resulting reaction mixture was stirred at room temperature for 1 h, then AcOH was evaporated, water (50 mL) was added, and product was extracted to MeTHF (3×10 mL). Combined organic phases were washed with saturated NaHCO$_3$ (3×10 mL), dried over MgSO$_4$, and concentrated to afford title compound as colorless oil (0.46 g, 90% yield).

MOTAM was also prepared through one-pot reaction starting from CLIN.

1. NaOMe, MeOH, r.t., 1 h
2. Na$_2$CO$_3$

AMAL

3. Tioureadioksid, Na$_2$CO$_3$
   H$_2$O, 60° C., 1 h
4. NaNO$_2$, AcOH
   r.t., 1 h

CLIN

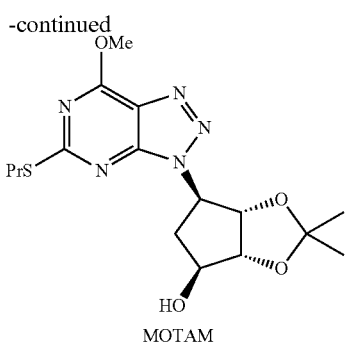

MOTAM

To a solution of CLIN (0.27 g, 1.0 mmol) in dry MeOH (5 mL) NaOMe (54 mg, 1.0 mmol) was added, and reaction mixture was then stirred at room temperature for 1 h. Then Et₃N (0.15 mL, 1.1 mmol) and AMAL (0.18 g, 1.05 mmol) were added, and reaction mixture was stirred at room temperature for 1 h. Then Na₂CO₃ (0.35 g, 3.3 mmol), formamidinesulfinic acid (0.36 g, 3.3 mmol) and water (0.5 mL) were added. Resulting reaction mixture was stirred at 60° C. for 1 h, then AcOH (10 mL) was slowly added, followed by NaNO₂ (76 mg, 1.1 mmol). Resulting reaction mixture was stirred at room temperature for 1 h, then volatile components were evaporated, water (40 mL) was added, and product was extracted to MeTHF (3×10 mL). Combined organic phases were washed with saturated NaHCO₃ (3×10 mL), dried over MgSO₄, and concentrated to afford crude product, which was purified by chromatography (SiO₂, hexane:EtOAc) to give MOTAM as colorless oil (0.20 g, 52% yield).

Example 10

Preparation of (3aR,4S,6R,6aS)-2,2-dimethyl-6-(5-(propylthio)-7-(2,2,2-trifluoroethoxy)-3H-[1,2,3]triazolo[4,5-d]pyrimidin-3-yl)tetrahydro-3aH-cyclopenta[d][1,3]dioxol-4-ol (FETAM)

A mixture of CLTAM (1.0 g, 2.59 mmol) and K₂CO₃ (0.39 g, 2.85 mmol) in 2,2,2-trifluoroethanol (3 mL) was stirred at room temperature for 1 hour. The solvent was evaporated, MeTHF (10 mL) was added, salts were filtered off, and filtrate was concentrated to afford crude product, which was then recrystallized from CH₂Cl₂/hexane mixture to give title compound as off white powder (1.01 g, 87% yield). MP 107° C.; MS (ESI) m/z: 450 [MH]⁺.

Example 11

Preparation of (3aR,4S,6R,6aS)-2,2-dimethyl-6-(5-(propylthio)-7-(2,2,2-trichloroethoxy)-3H-[1,2,3]triazolo[4,5-d]pyrimidin-3-yl)tetrahydro-3aH-cyclopenta[d][1,3]dioxol-4-ol (CETAM)

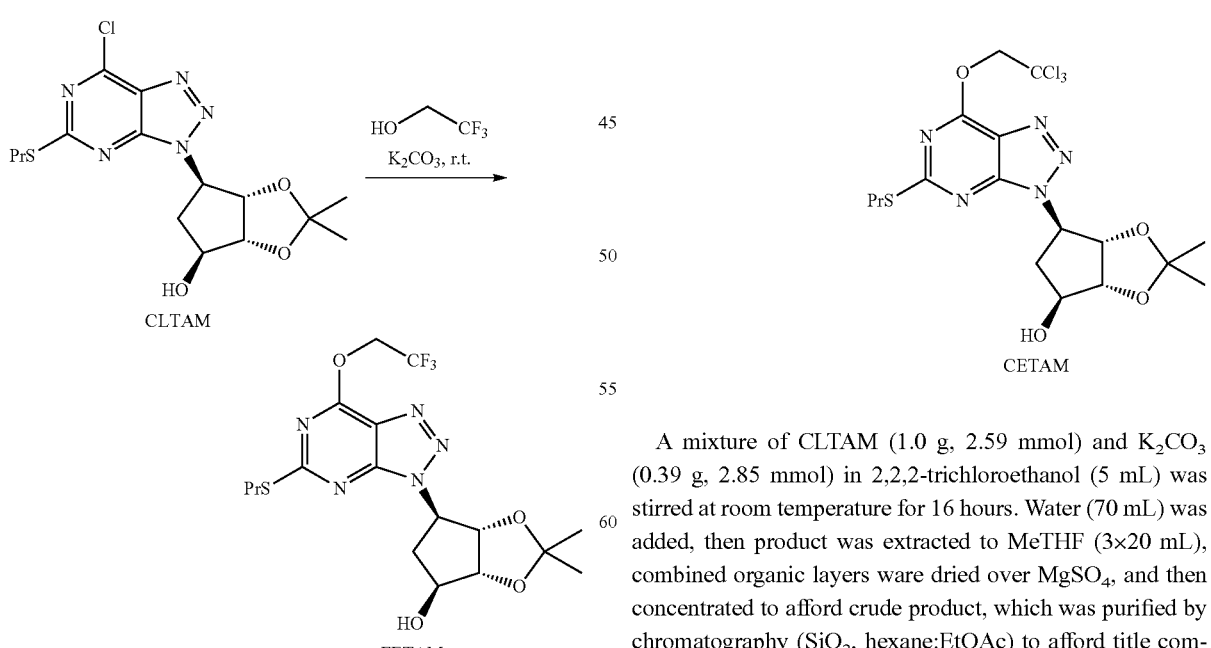

A mixture of CLTAM (1.0 g, 2.59 mmol) and K₂CO₃ (0.39 g, 2.85 mmol) in 2,2,2-trichloroethanol (5 mL) was stirred at room temperature for 16 hours. Water (70 mL) was added, then product was extracted to MeTHF (3×20 mL), combined organic layers ware dried over MgSO₄, and then concentrated to afford crude product, which was purified by chromatography (SiO₂, hexane:EtOAc) to afford title compound as white powder (1.00 g, 78% yield). MP 118° C.; MS (ESI) m/z: 498 [MH]⁺.

Example 12

Preparation of (3aR,4S,6R,6aS)-6-(7-ethoxy-5-(propylthio)-3H-[1,2,3]triazolo[4,5-d]pyrimidin-3-yl)-2,2-dimethyltetrahydro-3aH-cyclopenta[d][1,3]dioxol-4-ol (EOTAM)

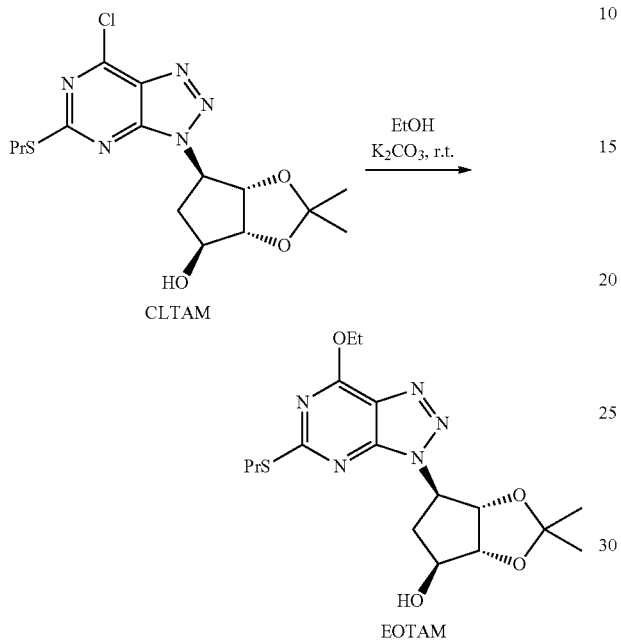

A mixture of CLTAM (1.0 g, 2.59 mmol) and K₂CO₃ (0.39 g, 2.85 mmol) in ethanol (5 mL) was stirred at room temperature for 16 hours. The solvent was evaporated, iPr₂O (10 mL) was added, salts were filtered off, and filtrate was concentrated to afford crude product, which was purified by chromatography (SiO₂, hexane:EtOAc) to afford title compound as colorless oil (1.00 g, 98% yield). MS (ESI) m/z: 396 [MH]⁺.

Example 13

Preparation of (3aR,4S,6R,6aS)-6-(7-(benzyloxy)-5-(propylthio)-3H-[1,2,3]triazolo[4,5-d]pyrimidin-3-yl)-2,2-dimethyltetrahydro-3aH-cyclopenta[d][1,3]dioxol-4-ol (BOTAM)

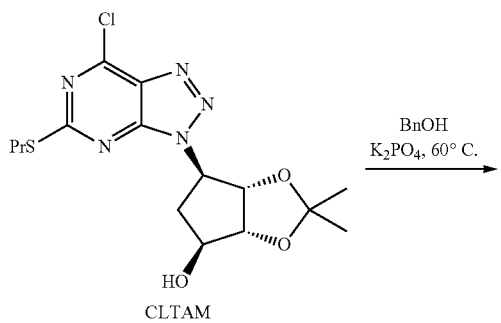

A mixture of CLTAM (2.0 g, 5.18 mmol), K₃PO₄ (1.21 g, 5.70 mmol) in benzyl alcohol (10 mL) was stirred at 70° C. for 88 hours. AcOH (2 mL) and water (50 mL) were added, then product was extracted to MeTHF (3×20 mL). Combined organic layers ware dried over MgSO₄, and then concentrated to afford crude product, which was purified by chromatography (SiO₂, hexane:EtOAc) to afford title compound as white powder (1.71 g, 72% yield). MP 97° C.; MS (ESI) m/z: 458 [MH]⁺.

Example 14

Preparation of (3aR,4S,6R,6aS)-2,2-dimethyl-6-(7-phenoxy-5-(propylthio)-3H-[1,2,3]triazolo[4,5-d]pyrimidin-3-yl)tetrahydro-3aH-cyclopenta[d][1,3]dioxol-4-ol (FOTAM)

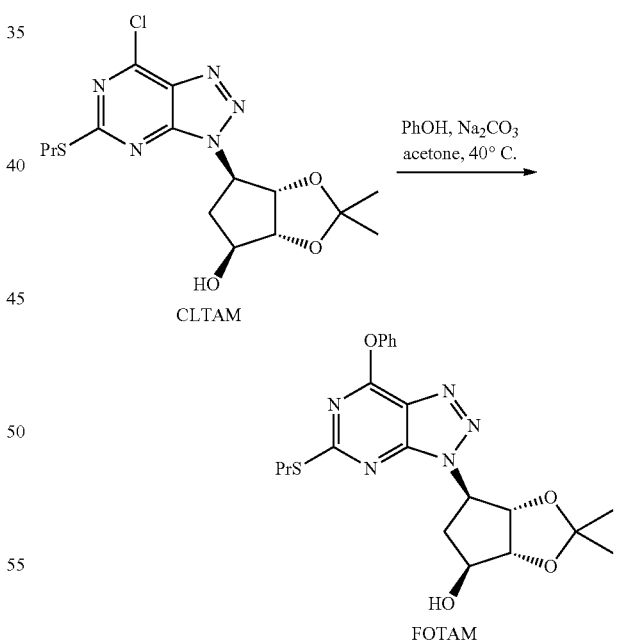

A mixture of CLTAM (1.76 g, 4.56 mmol), phenol (0.45 g, 4.79 mmol), and Na₂CO₃ (0.51 g, 4.79 mmol) in acetone (10 mL) was stirred at 40° C. for 16 hours, then salts were filtered off, and filtrate concentrated. AcOH (3 mL) and water (20 mL) were added, and product was extracted to MeTHF (3×10 mL). Combined organic layers ware dried over MgSO₄, and then concentrated to afford crude product, which was purified by chromatography (SiO₂, hexane:E- tOAc) to afford title compound as colorless oil (1.69 g, 83% yield). ¹H NMR (CDCl₃, 500 MHz) δ 0.81 (t, J=7.3 Hz, 3H), 1.30 (s, 3H), 1.49 (s, 3H), 1.53 (m, 2H), 2.32 (m, 1H), 2.82-2.89 (m, 3H), 4.36-4.42 (m, 2H), 4.77 (m, 1H), 5.01 (m, 1H), 5.33 (m, 1H), 7.23 (m, 2H), 7.27 (m, 1H), 7.39-7.43 (m, 2H); MS (ESI) m/z: 444 [MH]⁺.

Example 15

Preparation of (3aR,4S,6R,6aS)-6-(7-(4-methoxyphenoxy)-5-(propylthio)-3H-[1,2,3]triazolo-[4,5-d]pyrimidin-3-yl)-2,2-dimethyltetrahydro-3aH-cyclopenta[d][1,3]dioxol-4-ol (MFOTAM)

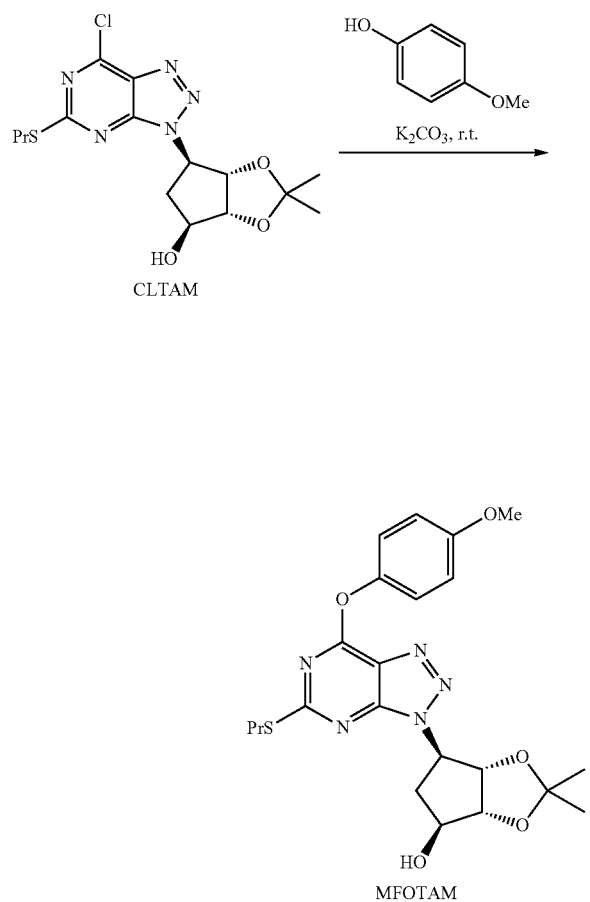

A mixture of CLTAM (3.09 g, 8 mmol), p-methoxyphenol (1.30 g, 10.5 mmol) and K₂CO₃ (1.44 g, 10.4 mmol) in 2-butanone (40 mL) was stirred 24 h at 25° C. The reaction mixture was washed with water (2×40 mL) and evaporated under reduced pressure. The residue was recrystallized from a toluene/cyclohexane mixture to give MFOTAM as an off-white powder (2.36 g, 62%): 99.2 area % HPLC; mp 114-116° C.; ¹H NMR (CDCl₃, 500 MHz) δ 0.90 (t, J=7.4 Hz, 3H), 1.34 (s, 3H), 1.55 (s, 3H), 1.61 (m, 2H), 2.19 (m, 1H), 2.32 (d, J=15.4 Hz, 1H), 2.90-2.97 (m, 3H), 3.86 (s, 3H), 4.45 (m, 1H), 4.83 (m, 1H), 4.99 (d, J=5.5 Hz, 1H), 5.40 (d, J=8.4 Hz, 1H), 6.97 (AA'XX', 2H), 7.20 (AA'XX', 2H).

Example 16

Preparation of (3aR,4S,6R,6aS)-2,2-dimethyl-6-(7-(naphthalen-2-yloxy)-5-(propylthio)-3H-[1,2,3]triazolo[4,5-d]pyrimidin-3-yl)tetrahydro-3aH-cyclopenta[d][1,3]dioxol-4-ol (NOTAM)

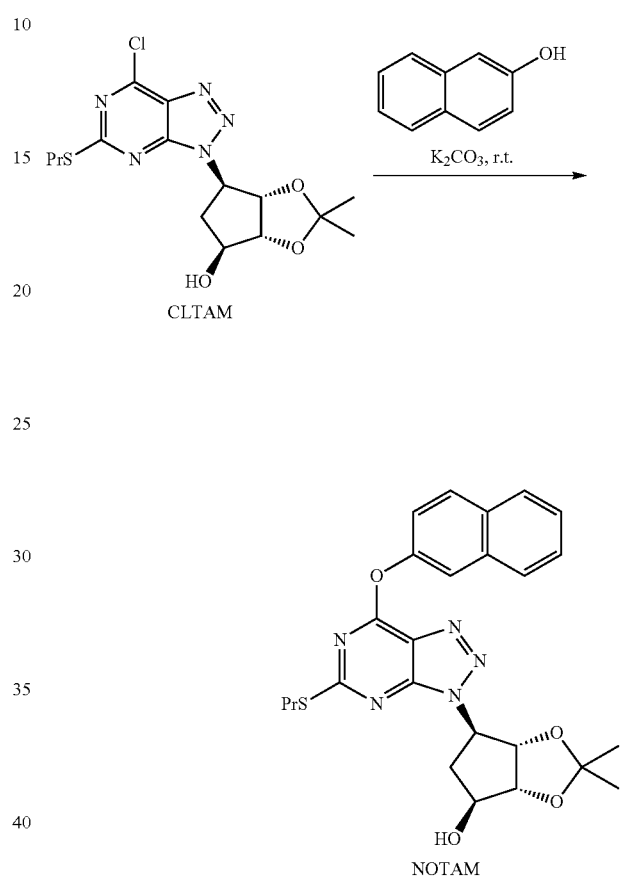

A mixture of CLTAM (3.09 g, 8 mmol), 2-naphthol (1.44 g, 10 mmol) and K₂CO₃ (1.44 g, 10.4 mmol) in acetonitrile (40 mL) was stirred 4 h at 25° C. The reaction mixture was diluted with water (200 mL), extracted with ethyl acetate (80 mL), the extract washed with water (100 mL) and evaporated under reduced pressure to give a crude solid product, which was triturated in warm cyclohexane (50 mL) and filtered. The product NOTAM was obtained as a pinkish powder (3.42 g, 87%): 98.9 area % HPLC; mp 147-149° C.; ¹H NMR (CDCl₃, 500 MHz) δ 0.70 (t, 3H, J=7.4 Hz), 1.36 (s, 3H), 1.53 (m, 2H), 1.56 (s, 3H), 2.35 (d, J=15.4 Hz, 1H), 2.86 (t, J=7.5 Hz, 2H), 2.96 (m, 1H), 4.45 (m, 2H), 4.85 (m, 1H), 5.04 (m, 1H), 5.43 (d, J=8.3 Hz, 1H), 7.43 (dd, J=8.8, 2.3 Hz, 1H), 7.55 (m, 2H), 7.76 (d, J=2.0 Hz, 1H), 7.87 (m, 1H), 7.90-7.97 (m, 2H); ¹³C NMR (CDCl₃, 500 MHz) δ 13.1, 22.7, 24.1, 26.6, 33.5, 37.2, 63.9, 76.7, 85.7, 87.8, 111.4, 118.7, 121.1, 124.0, 126.0, 126.7, 127.7, 127.8, 129.5, 131.7, 133.7, 149.3, 151.8, 160.1, 172.1; MS (ESI) m/z: 494 [MH]⁺.

Example 17

Preparation of (3aR,4S,6R,6aS)-2,2-dimethyl-6-(7-(naphthalen-1-yloxy)-5-(propylthio)-3H-[1,2,3]triazolo[4,5-d]pyrimidin-3-yl)tetrahydro-3aH-cyclopenta[d][1,3]dioxol-4-ol (ANOTAM)

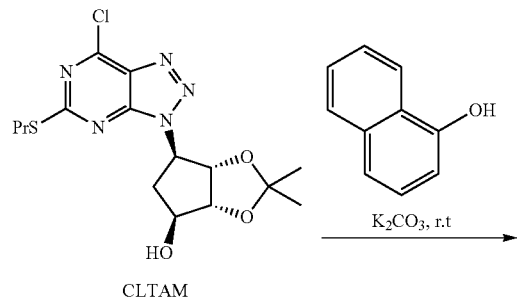

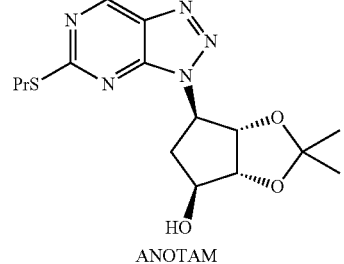

A mixture of CLTAM (3.09 g, 8 mmol), 1-naphthol (1.33 g, 9.2 mmol) and $K_2CO_3$ (1.44 g, 10.4 mmol) in 2-butanone (40 mL) was stirred 24 h at 25° C. The reaction mixture was washed with water (2×40 mL) and evaporated under reduced pressure. The residue was recrystallized from a diisopropyl ether/ethyl acetate mixture to give ANOTAM as an off-white powder (2.43 g, 62%): mp 137-139° C.; $^1$H NMR (CDCl$_3$, 500 MHz) δ 0.58 (t, J=7.3 Hz, 3H), 1.24 (m, 2H), 1.34 (s, 3H), 1.54 (s, 3H), 2.34 (d, J=15.4 Hz, 1H), 2.59 (t, J=7.4 Hz, 2H), 2.94 (m, 1H), 4.46 (m, 2H), 4.85 (m, 1H), 5.01 (m, 1H), 5.43 (d, J=8.4 Hz, 1H), 7.41 (dd, J=7.5, 0.7 Hz, 1H), 7.47 (td, J=6.9, 1.2 Hz, 1H), 7.51-7.57 (m, 2H), 7.86 (m, 2H), 7.93 (d, J=8.2 Hz, 1H); $^{13}$C NMR (CDCl$_3$, 500 MHz) δ 13.1, 22.6, 24.1, 26.6, 33.5, 37.2, 64.0, 76.8, 85.8, 87.8, 111.4, 118.1, 121.4, 123.8, 125.3, 126.61, 126.64, 126.7, 126.8, 128.0, 134.8, 147.8, 151.9, 160.4, 172.2; MS (ESI) m/z: 494 [MH]$^+$.

Example 18

Preparation of (3aR,4S,6R,6aS)-2,2-dimethyl-6-(7-(phenylthio)-5-(propylthio)-3H-[1,2,3]triazolo[4,5-d]pyrimidin-3-yl)tetrahydro-3aH-cyclopenta[d][1,3]dioxol-4-ol (TOTAM)

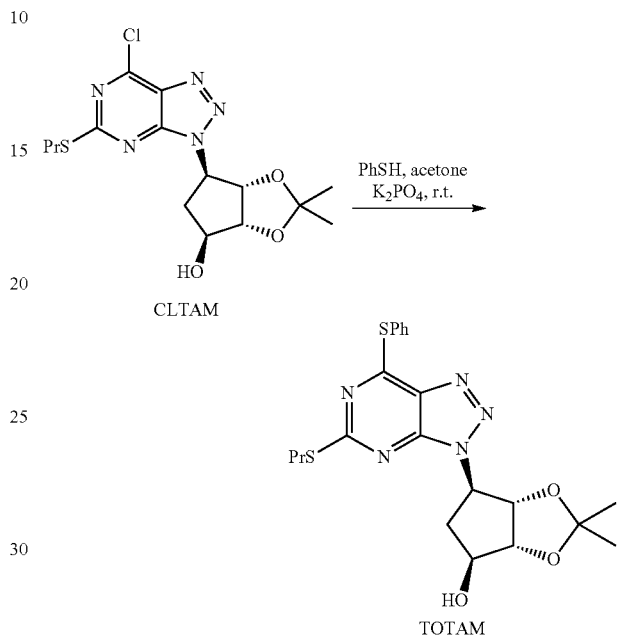

A mixture of CLTAM (1.0 g, 2.59 mmol), thiophenol (0.29 mL, 2.85 mmol), and $K_2CO_3$ (0.39 g, 2.85 mmol) in acetone (3 mL) was stirred at room temperature for 16 hours. Then volatile components were evaporated, iPr$_2$O (10 mL) was added, salts were filtered off, and filtrate was concentrated to afford crude product, which was purified by chromatography (SiO$_2$, hexane:EtOAc) to give title compound as colorless oil (0.95 g, 80% yield). MS (ESI) m/z: 460 [MH]$^+$.

Example 19

Preparation of 2-(3-((3aS,4R,6S,6aR)-6-hydroxy-2,2-dimethyltetrahydro-3aH-cyclopenta-[d][1,3]dioxol-4-yl)-5-(propylthio)-3H-[1,2,3]triazolo[4,5-d]pyrimidin-7-yl)isoindoline-1,3-dione (FATAM)

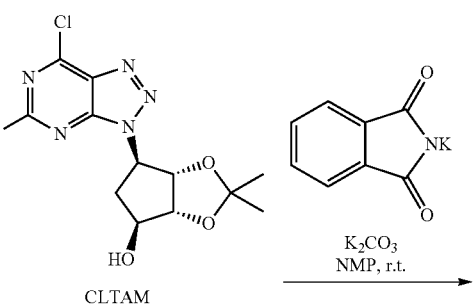

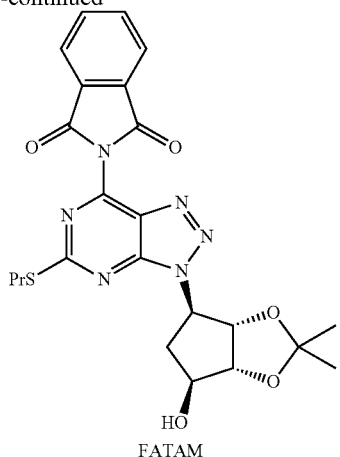

FATAM

A mixture of CLTAM (1.54 g, 4 mmol) and potassium phthalimidate (0.85 g, 4.6 mmol) in N-methylpyrrolidin-2-one (20 mL) was stirred 24 h at 25° C. The reaction mixture was diluted with water (80 mL), extracted with ethyl acetate (50 mL), the extract washed with water (2×30 mL) and evaporated under reduced pressure to give a crude product, which was further purified by flash chromatography to give FATAM as a crystalline solid (1.40 g, 70%): MS (ESI) m/z: 497 [MH]+.

Example 20

Preparation of (3aR,4S,6R,6aS)-6-(7-(1H-imidazol-1-yl)-5-(propylthio)-3H-[1,2,3]triazolo-[4,5-d]pyrimidin-3-yl)-2,2-dimethyltetrahydro-3aH-cyclopenta[d][1,3]dioxol-4-ol (IMTAM)

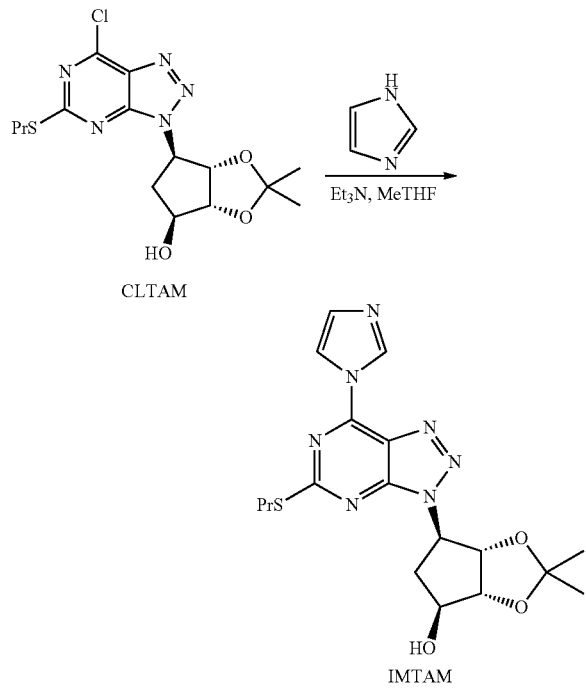

A mixture of CLTAM (1.16 g, 3.0 mmol), triethylamine (0.46 g, 4.5 mmol), imidazole (0.22 g, 3.3 mmol) and 2-methyltetrahydrofuran (5 mL) was stirred at 25° C. for 4 hours. Brine (10 mL) and water (10 mL) were added and the phases were separated. Organic phase was concentrated under reduced pressure and the product was purified by chromatography (SiO$_2$, hexane:EtOAc) to afford title compound (0.90 g, 72% yield). $^1$H NMR (CDCl$_3$): δ 1.10 (t, 3H; J=7.4 Hz), 1.33 (s, 3H), 1.53 (s, 3H), 1.84 (m, 2H), 2.44 (m, 1H), 2.87 (m, 1H), 3.22 (m, 2H), 4.30 (s, 1H), 4.44 (s, 1H), 4.80 (d, 1H; J=5.7 Hz), 5.18 (d, 1H; J=5.7 Hz), 5.34 (m, 1H), 7.23 (m, 1H), 8.31 (m, 1H), 9.09 (m, 1H).

Example 21

Preparation of methyl 2-(((3aR,4S,6R,6aS)-6-(7-methoxy-5-(propylthio)-3H-[1,2,3]triazolo-[4,5-d]pyrimidin-3-yl)-2,2-dimethyltetrahydro-3aH-cyclopenta[d][1,3]dioxol-4-yl)oxy)acetate (MOTAME)

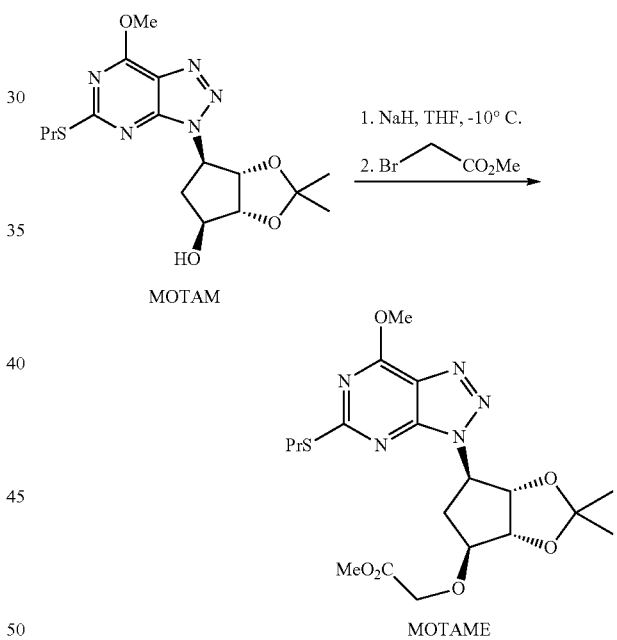

To a solution of MOTAM (1.0 g, 2.62 mmol) in dry THF (10 mL) NaH (60%, 0.12 g, 2.88 mmol) was added at −10° C. and stirred for 15 min, then methyl bromoacetate (0.27 mL, 2.88 mmol) was added at −10° C. Resulting reaction mixture was stirred at −10° C. for 2 h. Water was added (50 mL), and product was extracted to MeTHF (3×20 mL). Combined organic layers were dried over MgSO$_4$, and concentrated to afford crude product, which was then purified by chromatography (SiO$_2$, hexane:EtOAc) to afford colorless oil (0.95 g, 80% yield). $^1$H NMR (CDCl$_3$, 500 MHz) δ 1.09 (t, J=7.3 Hz, 3H), 1.35 (s, 3H), 1.55 (s, 3H), 1.83 (m, 2H), 2.74 (m, 2H), 3.19 (m, 2H), 3.73 (s, 3H), 4.13 (s, 3H), 4.22 (s, 3H), 4.83 (dd, J=6.9, 2.6 Hz, 1H), 5.16 (m, 1H), 5.31 (s, 3H), 5.50 (dd, J=6.9, 3.8 Hz, 1H); MS (ESI) m/z: 454 [MH]+.

Example 22

Preparation of isopropyl 2-(((3aR,4S,6R,6aS)-6-(7-methoxy-5-(propylthio)-3H-[1,2,3]triazolo[4,5-d]pyrimidin-3-yl)-2,2-dimethyltetrahydro-3aH-cyclopenta[d][1,3]dioxol-4-yl)oxy)acetate (MOTAMEI)

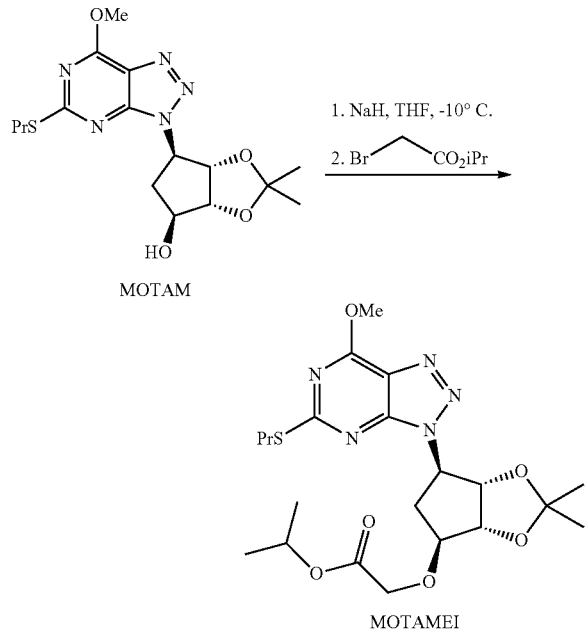

To a solution of MOTAM (3.81 g, 10.0 mmol) in dry THF (10 mL) NaH (60%, 0.44 g, 11.0 mmol) was added at −10° C. and stirred for 15 min, then isopropyl bromoacetate (1.42 mL, 11.0 mmol) was added at −10° C. Resulting reaction mixture was stirred at −10° C. for 16 h. Acetic acid (5 mL) and water (50 mL) were added, and product was extracted to MeTHF (3×20 mL). Combined organic layers were dried over MgSO$_4$, and concentrated to afford crude product, which was then purified by chromatography (SiO$_2$, hexane:EtOAc) to afford colorless oil (3.88 g, 81% yield). MS (ESI) m/z: 482 [MH]$^+$.

Example 23

Preparation of methyl 2-(((3aR,4S,6R,6aS)-6-(7-(benzyloxy)-5-(propylthio)-3H-[1,2,3]triazolo[4,5-d]pyrimidin-3-yl)-2,2-dimethyltetrahydro-3aH-cyclopenta[d][1,3]dioxol-4-yl)oxy)acetate (BOTAME)

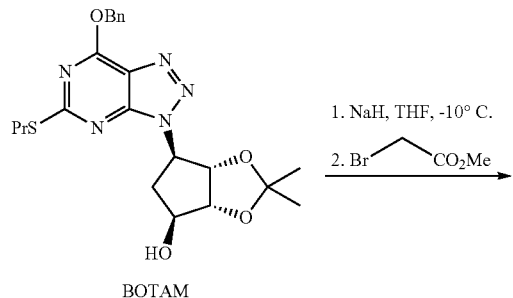

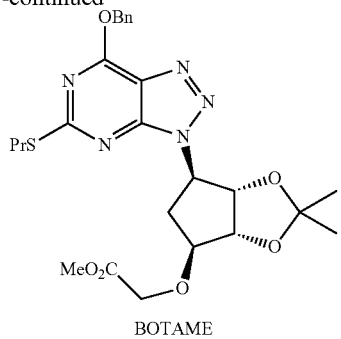

To a solution of BOTAM (1.0 g, 2.19 mmol) in dry THF (10 mL) NaH (60%, 105 mg, 2.63 mmol) was added at −10° C. and stirred for 15 min, then methyl bromoacetate (0.25 mL, 2.63 mmol) was added at −10° C. Resulting reaction mixture was stirred at −10° C. for 2 h. Acetic acid (1 mL) and water (50 mL) were added, and product was extracted to MeTHF (3×20 mL). Combined organic layers were dried over MgSO$_4$, and concentrated to afford crude product, which was then purified by chromatography (SiO$_2$, hexane:EtOAc) to afford colorless syrup (0.87 g, 78% yield). MS (ESI) m/z: 530 [MH]$^+$.

Example 24

Preparation of isopropyl 2-(((3aR,4S,6R,6aS)-6-(7-(naphthalen-2-yloxy)-5-(propylthio)-3H-[1,2,3]triazolo[4,5-d]pyrimidin-3-yl)-2,2-dimethyltetrahydro-3aH-cyclopenta[d][1,3]dioxol-4-yl)oxy)acetate (NOTAMEP)

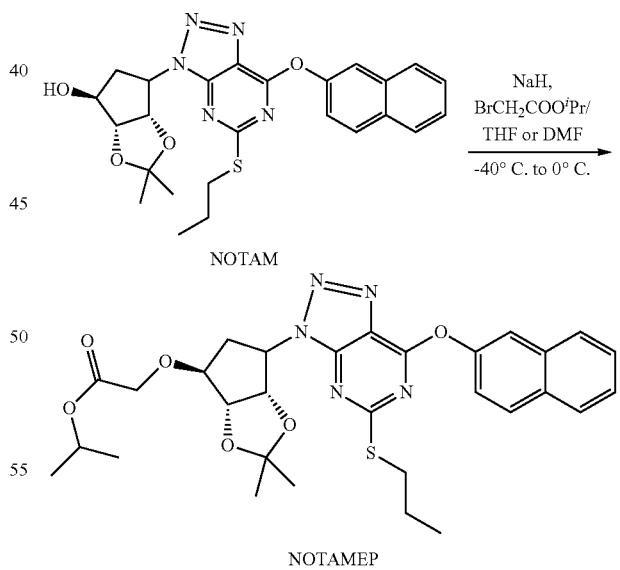

To a solution of NOTAM (0.99 g, 2 mmol) and isopropyl bromoacetate (0.39 mL, 3 mmol) in dried THF (20 mL) cooled to −40° C. was added 60% sodium hydride (0.12 g, 3 mmol). The temperature was raised to 0° C. during the course of 3 h and then the reaction was quenched with acetic acid (0.5 mL), diluted with water (60 mL) and extracted with diethyl ether (60 mL). The organic phase was washed with water (60 mL) and concentrated to give a crude product which was analyzed by LC-MS (ESI), which shows 6 area % of a component with m/z=594 [MH]+ corresponding to the expected product NOTAMEP and a major component with m/z=245 [MH]+ corresponding to isopropyl 2-(naphthalen-2-yloxy)acetate which as a product of alkylation of the cleaved naphthalen-2-yloxy group of a side reaction.

The yield was improved to 43 area % of the desired product with m/z=594 [MH]+ by using the same volume of DMF instead of THF.

Example 25

Preparation of 2-(((3aR,4S,6R,6aS)-6-(7-methoxy-5-(propylthio)-3H-[1,2,3]triazolo[4,5-d]pyrimidin-3-yl)-2,2-dimethyltetrahydro-3aH-cyclopenta[d][1,3]dioxol-4-yl)oxy)ethanol

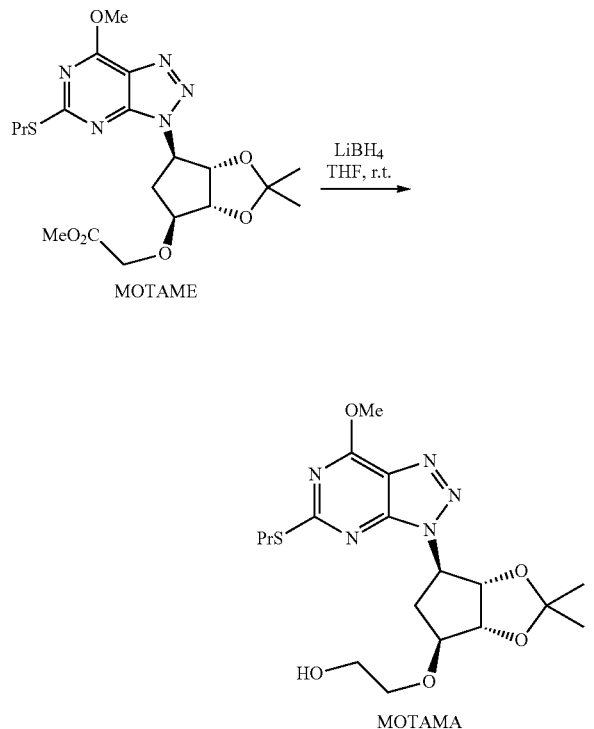

To a solution of MOTAME (0.85 g, 1.87 mmol) in dry THF (15 mL) at 0° C. LiBH$_4$ (90 mg, 4.12 mmol) was added, and resulting reaction mixture was stirred at room temperature for 16 h. Reaction was then quenched by slow addition of AcOH (5 mL), water was added (50 mL), and product was extracted to MeTHF (3×30 mL). Combined organic layers ware dried over MgSO$_4$, and then concentrated to afford crude product, which was purified by chromatography (SiO$_2$, hexane:EtOAc) to afford title compound as colorless oil (0.73 g, 92% yield). $^1$H NMR (CDCl$_3$, 500 MHz) δ 1.09 (t, J=7.3 Hz, 3H), 1.37 (s, 3H), 1.55 (s, 3H), 1.83 (m, 2H), 2.23 (m, 1H), 2.52 (m, 1H), 2.68 (m, 1H), 3.20 (m, 2H), 3.50 (m, 1H), 3.52-3.65 (m, 3H), 4.03 (m, 1H), 4.22 (s, 3H), 4.89 (m, 1H), 5.20 (m, 1H), 5.56 (m, 1H); MS (ESI) m/z: 426 [MH]+.

Example 26

Preparation of 2-(((3aR,4S,6R,6aS)-6-(7-methoxy-5-(propylthio)-3H-[1,2,3]triazolo[4,5-d]pyrimidin-3-yl)-2,2-dimethyltetrahydro-3aH-cyclopenta[d][1,3]dioxol-4-yl)oxy)ethanol (MOTAMA) Through One-Pot Reaction Starting from MOTAM

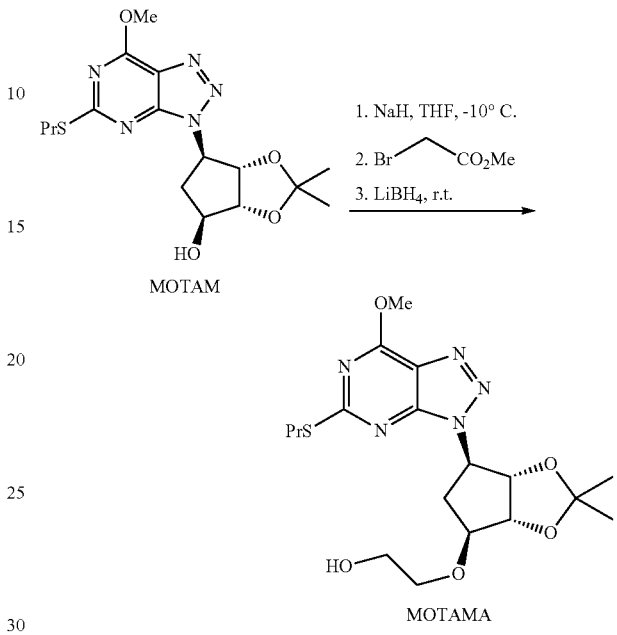

To a solution of MOTAM (1.8 g, 4.72 mmol) in dry THF (20 mL) NaH (60%, 0.23 g, 5.66 mmol) is added at −10° C. and stirred for 15 min, then methyl bromoacetate (0.54 mL, 5.66 mmol) is added at −10° C. Resulting reaction mixture is stirred at −10° C. for 2 h, then LiBH$_4$ (0.21 g, 9.44 mmol) was added, and resulting reaction mixture was stirred at room temperature for 2 h. Reaction was then quenched by slow addition of AcOH (2 mL), water was added (100 mL), and product was extracted to MeTHF (3×30 mL). Combined organic layers were dried over MgSO$_4$, and then concentrated to afford crude product, which was purified by chromatography (SiO$_2$, hexane:EtOAc) to afford title compound as colorless oil (1.52 g, 76% yield). $^1$H NMR (CDCl$_3$, 500 MHz) δ 1.09 (t, J=7.3 Hz, 3H), 1.37 (s, 3H), 1.55 (s, 3H), 1.83 (m, 2H), 2.23 (m, 1H), 2.52 (m, 1H), 2.68 (m, 1H), 3.20 (m, 2H), 3.50 (m, 1H), 3.52-3.65 (m, 3H), 4.03 (m, 1H), 4.22 (s, 3H), 4.89 (m, 1H), 5.20 (m, 1H), 5.56 (m, 1H); MS (ESI) m/z: 426 [MH]+.

Example 27

Preparation of 2-(((3aR,4S,6R,6aS)-6-(7-(benzyloxy)-5-(propylthio)-3H-[1,2,3]triazolo[4,5-d]pyrimidin-3-yl)-2,2-dimethyltetrahydro-3aH-cyclopenta[d][1,3]dioxol-4-yl)oxy)ethanol

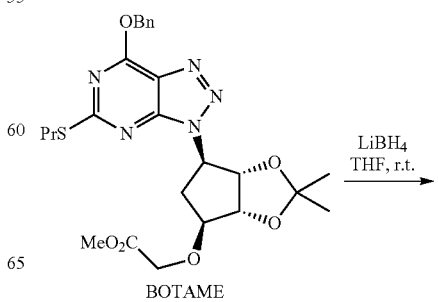

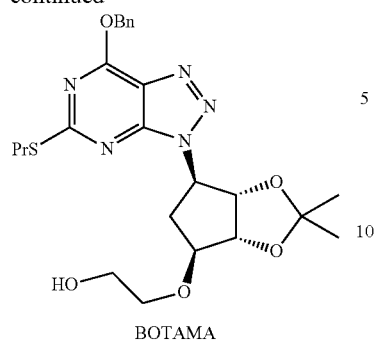

BOTAMA

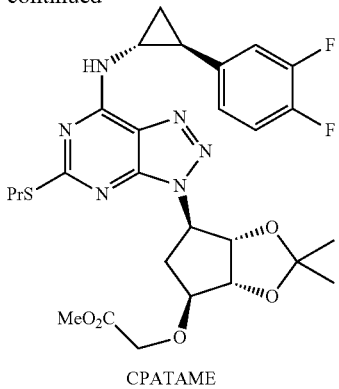

CPATAME

To a solution of BOTAME (0.80 g, 1.51 mmol) in dry THF (10 mL) at room temperature LiBH$_4$ (66 mg, 3.02 mmol) was added, and resulting reaction mixture was stirred at room temperature for 1 h. Reaction was then quenched by slow addition of AcOH (2 mL), water was added (20 mL), and product was extracted to EtOAc (3×10 mL). Combined organic layers were dried over MgSO$_4$, and then concentrated to afford crude product, which was purified by chromatography (SiO$_2$, hexane:EtOAc) to afford title compound as colorless oil (0.61 g, 81% yield). $^1$H NMR (CDCl$_3$, 500 MHz) δ 1.09 (t, J=7.3 Hz, 3H), 1.37 (s, 3H), 1.55 (s, 3H), 1.83 (m, 2H), 2.23 (m, 1H), 2.52 (m, 1H), 2.68 (m, 1H), 3.20 (m, 2H), 3.50 (m, 1H), 3.52-3.65 (m, 3H), 4.03 (m, 1H), 4.22 (s, 3H), 4.89 (m, 1H), 5.20 (m, 1H), 5.56 (m, 1H); MS (ESI) m/z: 502 [MH]$^+$.

A solution of MOTAME (1.0 g, 2.21 mmol) and CPA (0.41 g, 2.43 mmol) in MeOH (10 mL) was stirred at 60° C. until TLC showed total conversion (several days). Water was added (50 mL), and product was extracted to MeTHF (3×10 mL). Combined organic layers were dried over MgSO$_4$, and concentrated to afford crude product, which was then purified by chromatography (SiO$_2$, hexane:EtOAc) to afford colorless syrup (0.26 g, 20% yield). MS (ESI) m/z: 591 [MH].

Example 29

Preparation of 2-(((3aR,4S,6R,6aS)-6-(7-(((1R,2S)-2-(3,4-difluorophenyl)cyclopropyl)-amino)-5-(propylthio)-3H-[1,2,3]triazolo[4,5-d]pyrimidin-3-yl)-2,2-dimethyltetrahydro-3aH-cyclopenta[d][1,3]dioxol-4-yl)oxy)ethanol (CPATAMA) from MOTAMA Example 28

Preparation of methyl 2-(((3aR,4S,6R,6aS)-6-(7-(((1R,2S)-2-(3,4-difluorophenyl)cyclo-propyl)amino)-5-(propylthio)-3H-[1,2,3]triazolo[4,5-d]pyrimidin-3-yl)-2,2-dimethyl-tetrahydro-3aH-cyclopenta[d][1,3]dioxol-4-yl)oxy)acetate (CPATAME)

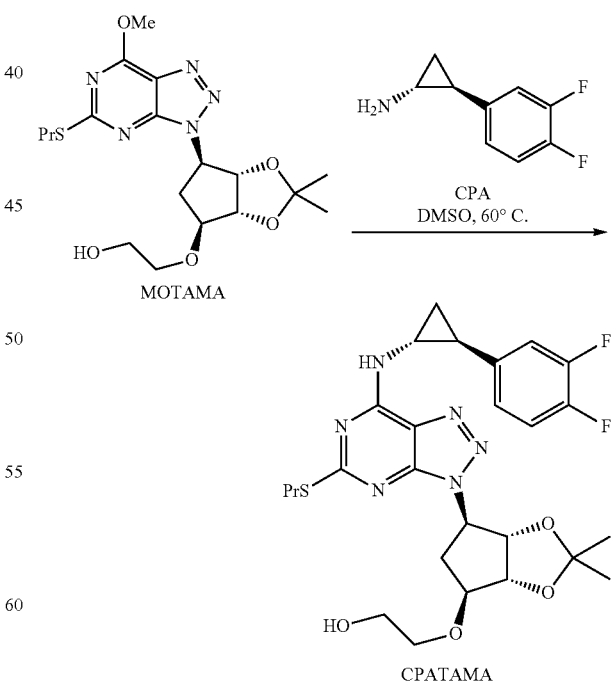

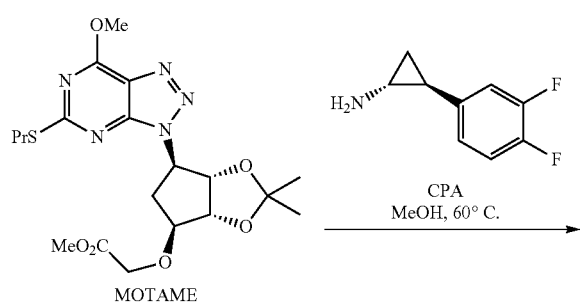

To a solution of MOTAMA (0.70 g, 1.65 mmol) in dry DMSO (5 mL) at room temperature CPA (0.29 g, 1.73 mmol) was added and reaction mixture was stirred at 60° C.

for 16 h. Water was added (50 mL), and product was extracted to MeTHF (3×10 mL). Combined organic layers were dried over MgSO$_4$, and concentrated to afford crude product, which was then purified by chromatography (SiO$_2$, hexane:EtOAc) to afford colorless syrup (0.72 g, 78% yield). MS (ESI) m/z: 563 [MH]$^+$.

Example 30

Preparation of 2-(((3aR,4S,6R,6aS)-6-(7-(((1R,2S)-2-(3,4-difluorophenyl)cyclopropyl)-amino)-5-(propylthio)-3H-[1,2,3]triazolo[4,5-d]pyrimidin-3-yl)-2,2-dimethyltetrahydro-3aH-cyclopenta[d][1,3]dioxol-4-yl)oxy)ethanol (CPATAMA) from BOTAMA

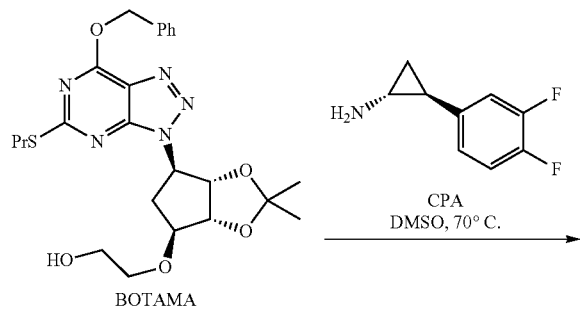

To a solution of BOTAMA (0.20 g, 0.40 mmol) in dry DMSO (2 mL) at room temperature CPA (74 mg, 0.44 mmol) was added and reaction mixture was stirred at 70° C. for 3 days. Water was added (20 mL), and product was extracted to MeTHF (3×5 mL). Combined organic layers were dried over MgSO$_4$, and concentrated to afford crude product, which was then purified by chromatography (SiO$_2$, hexane:EtOAc) to afford colorless syrup (0.16 g, 72% yield). MS (ESI) m/z: 563 [MH]$^+$.

Example 31

Preparation of (1S,2S,3R,5S)-3-(7-(((1R,2S)-2-(3,4-difluorophenyl)cyclopropyl)amino)-5-(propylthio)-3H-[1,2,3]triazolo[4,5-d]pyrimidin-3-yl)-5-(2-hydroxyethoxy)cyclopentane-1,2-diol (TCG)

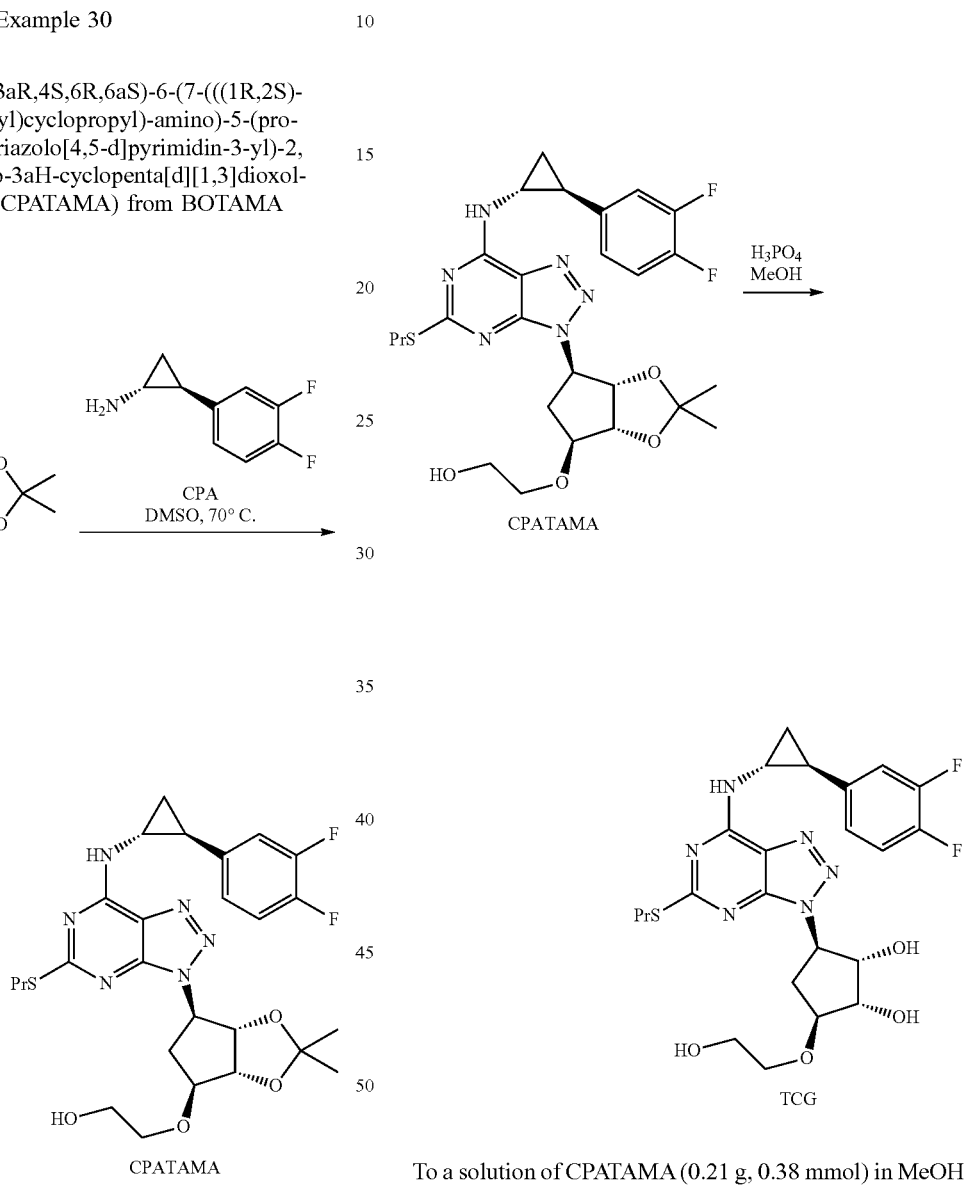

To a solution of CPATAMA (0.21 g, 0.38 mmol) in MeOH (10 mL) at room temperature ortho-phosphoric acid (85%, 1.5 mL) was slowly added. Resulting reaction mixture was stirred at room temperature for 24 h, then water was added (20 mL), and reaction mixture was neutralized with 1 M NaOH. Product was extracted to EtOAc (5×10 mL), combined organic phases were dried over Na$_2$SO$_4$, then concentrated to afford crude product, which was purified by chromatography (SiO$_2$, EtOAc) to afford title compound as a white powder (0.18 g, 90% yield). $^{19}$F NMR (CD$_3$OD, 470.5 MHz) δ−141.9−−142.1 (m, 1F), −145.6−−145.9 (m, 1F); MS (ESI) m/z: 523 [MH]$^+$.

The invention claimed is:

1. A process for the preparation of a compound of formula XI

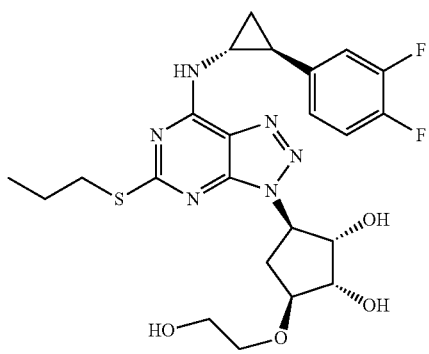

or a salt thereof,
comprising the steps of
(i) preparing a compound of formula VIII

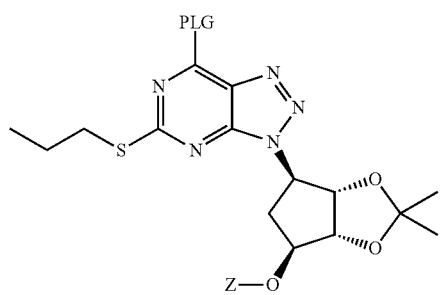

by
(a) providing a compound of formula VII

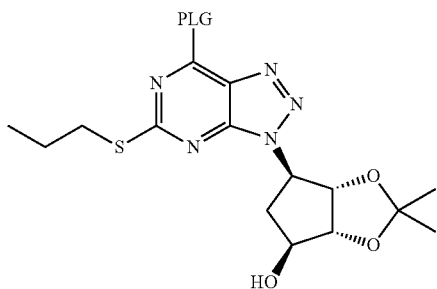

and
(b) O-alkylating the compound of formula VII to obtain the compound of formula VIII,
wherein PLG is methoxy or benzyloxy, and Z is hydroxyethyl or a group convertible to hydroxyethyl,
(ii) reacting a compound of formula VIII with a compound of formula IX

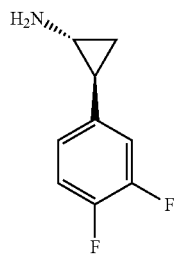

(iii) carrying out deprotection reaction to remove the vicinal hydroxyl protecting group at the pentane ring,
(iv) optionally converting group Z, if not hydroxyethyl, into hydroxyethyl, and
(v) optionally forming a salt of the compound of formula XI.

2. A process for the preparation of a pharmaceutical composition comprising a compound of formula XI or a salt thereof

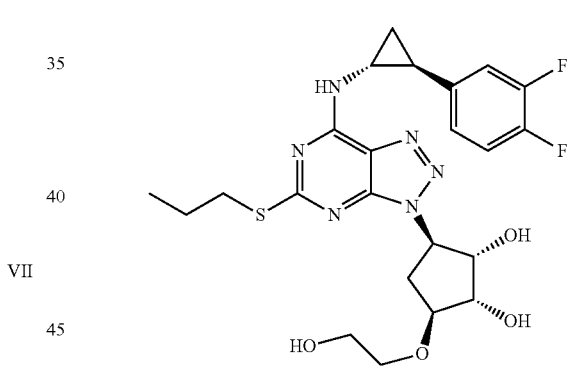

comprising the steps of:
(i) preparing a compound of formula XI or a salt thereof according to claim 1, and
(ii) mixing the compound of formula XI or a salt thereof with a pharmaceutically acceptable carrier and/or excipient.

* * * * *